United States Patent [19]
Krishnamurthy et al.

[11] Patent Number: 6,015,657
[45] Date of Patent: ***Jan. 18, 2000

[54] PHOTOGRAPHIC ELEMENTS CONTAINING 2-EQUIVALENT PYRAZOLONE COUPLERS AND PROCESS FOR THEIR USE

[75] Inventors: Sundram Krishnamurthy, Penfield, N.Y.; Michael William Crawley, Herts, United Kingdom; David Scott Bailey; John Lawrence Pawlak, both of Rochester, N.Y.

[73] Assignee: Eastman Kodak Company, Rochester, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 08/179,473

[22] Filed: Jan. 10, 1994

Related U.S. Application Data

[63] Continuation-in-part of application No. 07/905,052, Jun. 26, 1992, abandoned, which is a continuation-in-part of application No. 07/731,671, Jul. 17, 1991, abandoned.

[51] Int. Cl.[7] ..................................... G03C 1/73
[52] U.S. Cl. ........................ 430/554; 430/386; 430/387; 430/555; 430/558
[58] Field of Search .................................. 430/551, 554, 430/555, 558

[56] References Cited

U.S. PATENT DOCUMENTS

| | | | |
|---|---|---|---|
| 4,351,897 | 9/1982 | Aoki et al. | 430/555 |
| 4,413,054 | 11/1983 | Mitsui et al. | 430/555 |
| 4,740,438 | 4/1988 | Krishnamurthy | 430/17 |
| 4,853,319 | 8/1989 | Krishnamurthy et al. | 430/387 |
| 4,900,657 | 2/1990 | Crawley et al. | 430/555 |
| 5,200,309 | 4/1993 | Merkel et al. | 430/555 |

FOREIGN PATENT DOCUMENTS 60-057839 of 0000 Japan .

*Primary Examiner*—Hoa Van Le
*Attorney, Agent, or Firm*—Arthur E. Kluegel

[57] ABSTRACT

A photographic element contains at least one photosensitive silver halide emulsion layer having associated therewith a 5-pyrazolone photographic coupler represented by the formula:

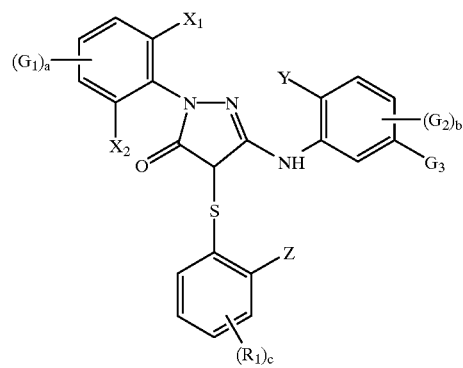

wherein substituents $X_1$, $X_2$, $Y$, $G_1$, $G_2$, $G_3$, $Z$, and $R_1$ may be as specified in the specification; a, b, and c are individually integers form 0 to 3 provided that "a" cannot be an integer which, combined with the selection of $X_1$ and $X_2$, allows the number of chloride substituents on the ring containing $G_1$ to exceed 3; and the sum of the Hammett's sigma values for $X_1$, $X_2$, $Y$, $G_1$, $G_2$, and $G_3$ is at least 1.3.

19 Claims, No Drawings

PHOTOGRAPHIC ELEMENTS CONTAINING 2-EQUIVALENT PYRAZOLONE COUPLERS AND PROCESS FOR THEIR USE

CROSS-REFERENCE TO RELATED APPLICATIONS

This application is a continuation-in-part of U.S. Ser. No. 07/905,052 filed Jun. 26, 1992, now abandoned, which is, in turn, a continuation-in-part of U.S. Ser. No. 07/731,671 filed Jul. 17, 1991, now abandoned.

BACKGROUND OF THE INVENTION

This invention relates to pyrazolone magenta dye-forming couplers having a particular thio coupling-off group that enables improved photographic properties and to photographic materials and processes comprising such couplers.

In color photographic silver halide materials and processes pyrazolone couplers comprising arylthio coupling-off groups have provided magenta dye images having useful properties. Examples of such compounds are described in, for example, U.S. Pat. No. 4,413,054, Japanese published patent application 60/057839, U.S. Pat. Nos. 4,900,657 and 4,351,897. An example of such a pyrazolone coupler described in, for example, U.S. Pat. No. 4,413,054 is designated herein as comparison coupler C-1 and is represented by the formula:

C-1

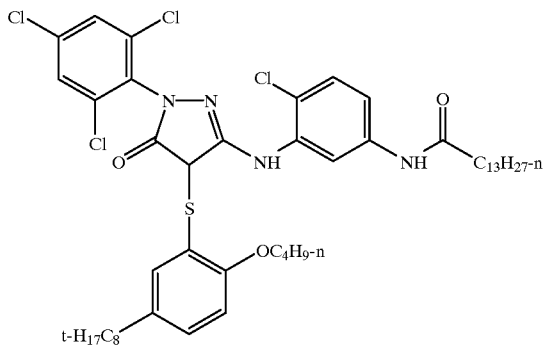

Coupler C-1 has not been entirely satisfactory due to the formation of undesired stain in a color photographic silver halide element upon exposure and processing and because it does not provide the desired image-dye density upon rapid machine processing. The coupler C-1 does not achieve full dye density, especially when the exposed color photographic element is machine processed without the presence of Lippman fine grain silver halide being present in the photographic element. It has been desirable to reduce or avoid the need for added Lippman fine grain silver halide without diminishing dye density in the processed color photographic silver halide element.

Another example of a pyrazolone coupler known to the art is described in U.S. Pat. No. 4,853,319 is designated herein as comparison coupler C-2 and is represented by the formula:

C-2

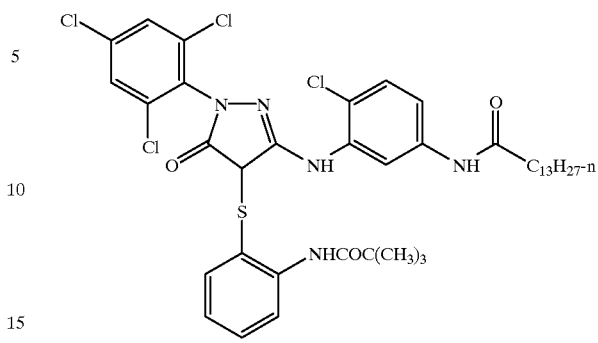

The presence of an acylamine group in the ortho position on the phenylthio coupling-off group of coupler C-2 has provided advantageous properties. This coupler does not require Lippman fine grain silver halide in order to obtain adequate dye density upon rapid machine processing. However, the coupling activity of both couplers C-1 and C-2 is unacceptably reduced in the presence of polyvalent cations, especially calcium ion, which leads to a reduction of the color density of the green record. Further, the hue of the resultant dyes from these two couplers is too hypsochromic to give good color reproduction. Another problem of certain types of arylthiopyrazolone couplers is extremely poor solubility in photographic coupler solvents. The poor solubility necessitates the use of auxiliary solvents which then have to be removed through an undesirable additional washing step.

U.S. Pat. No. 4,942,116, to Renner (Counterpart to DE 3,730,557) teaches 3 anilino pyrazolones with a broad array of arylthio coupling-off groups containing an alkyl substituent in the ortho position. The products are, however, concerned with light stability of dye images in color prints and not the features described for this invention. Moreover, the only examples that provide a sigma of 1.3 as provided for herein utilize cyanide as an electron withdrawing agent. Cyanide substituents are not within this invention because of their notorious light instability (see for example EP 439, 069).

U.S. Pat. No. 4,740,438 teaches the use of organic disulfides as image dye light stabilizers with couplers such as C-10. This type of coupler is characterized by having a 5-sulfamoyl ballast in the 3-anilino ring of the pyrazolone. As demonstrated in the examples, the dye from this coupler has unacceptable hue for adequate color reproduction, especially that of reds.

C-10

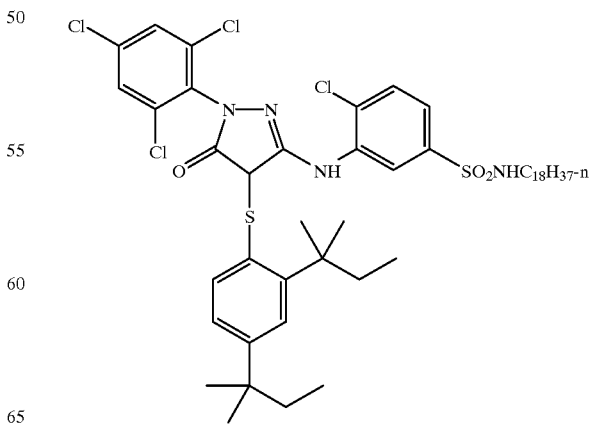

Another type of coupler that has been considered is one having a pentachloro-substitution on the N phenyl ring (U.S. Pat. No. 4,876,182). While such materials provide advantageous properties they are not preferred because rings containing more than 3 chloro substituents present laborious and costly administrative efforts relative to disposal.

It has been desired to provide a new pyrazolone coupler having an arylthio coupling-off group in a color photographic silver halide element and process which is capable of forming a magenta dye image of good dye hue and stability, with high dye yield based on rapid machine processing, and with reduction or omission of Lippman fine grain silver halide in the element. Also, it has been desired to provide such 2-equivalent pyrazolone couplers with adequate solubility/dispersibility characteristics, so that the couplers can be easily incorporated into color photographic silver halide elements. Further, it has been desired to reduce the sensitivity of arylthiopyrazolone couplers toward changes in polyvalent cation levels, especially calcium ion, in the processing of photographic elements. Additionally, it has been desired to provide a multilayer photographic element containing such a coupler which exhibits improved acutance and granularity.

SUMMARY OF THE INVENTION

It has now been found that superior photographic properties are provided by a photographic element comprising at least one photosensitive silver halide emulsion layer having associated therewith a 5-pyrazolone photographic coupler represented by the formula:

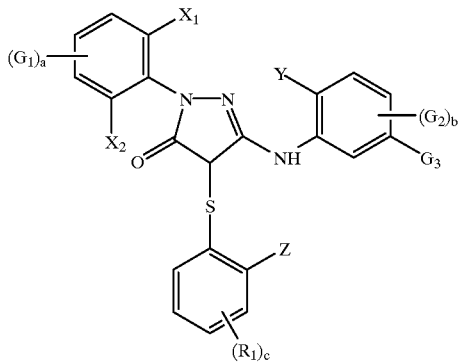

wherein:
a) substituents $X_1$, $X_2$, Y, $G_1$ and $G_2$ are individually selected from the group consisting of halogen, alkyl, alkoxy, aryloxy, acylamino, alkylthio, arylthio, sulfonamido, sulfamoyl, sulfamido, carbamoyl, diacylamino, alkoxycarbonyl, aryloxycarbonyl, alkoxysulfonyl, aryloxysulfonyl, alkylsulfonyl, arylsulfonyl, alkylsulfinyl, arylsulfinyl, alkoxycarbonylamino, aryloxycarbonylamino, alkylureido, arylureido, acyloxy, nitro, trifluoromethyl and carboxy and, in the case of $X_1$, $X_2$, and Y, hydrogen;
b) a, b, and c are individually integers form 0 to 3 provided that "a" cannot be an integer which, combined with the selection of $X_1$ and $X_2$, allows the number of chloride substituents on the ring containing $G_1$ to exceed 3;
c) $G_3$ is selected from the group consisting of hydrogen, halogen, acylamino, sulfonamido, sulfamido, carbamoyl, diacylamino, alkoxycarbonyl, aryloxycarbonyl, alkoxysulfonyl, aryloxysulfonyl, alkylsulfonyl, arylsulfonyl, alkylsulfinyl, arylsulfinyl, alkoxycarbonylamino, aryloxycarbonylamino, alkylureido, arylureido, acyloxy, trifluoromethyl and carboxyl;
d) $R_1$ is selected from the group consisting of $G_1$ and hydroxyl;
e) Z is an alkyl group containing at least 3 carbon atoms; and
f) the sum of the Hammett's sigma values for $X_1$, $X_2$, Y, $G_1$, $G_2$, and $G_3$ is at least 1.3.

Hammett's sigma rules are well known and the values for these constants can be easily found in the published literature (C. Hansch and A. J. Leo, in "Substituent Constants for Correlation Analysis in Chemistry and Biology", Wiley, New York, 1979; Albert J. Leo, in "Comprehensive Medicinal Chemistry", edited by C. Hansch, P. G. Sammes, and J. B. Taylor, Pergamon Press, New York, Volume 4, 1990. "The Chemists' Companion", A. J. Gordon and R. A. Ford, John Wiley & Sons, New York, 1972 and "Progress in Physical Organic Chemistry", V.13, R. W. Taft, Ed., John Wiley & Sons, New York.) Generally, sigma increases with increasing electron withdrawing power of the substituent (with hydrogen=zero). For Hammett's sigma values, only the atoms close to the ring have an electron withdrawing effect and remote atoms have no effect.

DETAILED DESCRIPTION OF THE INVENTION

Examples of $G_1$, $G_2$, $X_1$, $X_2$, Y, and $R_1$ include halogen, such as chlorine, bromine or fluorine; alkyl, including straight or branched chain alkyl, such as alkyl containing 1 to 30 carbon atoms, for example methyl, trifluoromethyl, ethyl, t-butyl, and tetradecyl; alkoxy, such as alkoxy containing 1 to 30 carbon atoms, for example methoxy, ethoxy, propoxy, butoxy, 2-methoxyethoxy, sec-butoxy, hexyloxy, 2-ethylhexyloxy, tetradecyloxy 2-(2,4-di-t-pentylphenoxy) ethoxy, and 2-dodecyloxyethoxy; aryloxy, such as phenoxy, alpha- or beta-naphthyloxy, and 4-tolyloxy; acylamino, such as acetamido, benzamido, butyramido, tetradecanamido, alpha-(2,4-di-t-pentylphenoxy)acetamido, alpha-(2,4-di-t-pentylphenoxy)butyramido, alpha-(3-pentadecylphenoxy) hexanamido, alpha-(4-hydroxy-3-t-butylphenoxy) tetradecanamido, 2-oxo-pyrrolidin-1-yl, 2-oxo-5-tetradecyl-pyrrolin-1-yl, N-methyl-tetradecanamido, and t-butylcarbonamido; sulfonamido, such as methylsulfonamido, benzenesulfonamido, p-toluylsulfonamido, p-dodecyl-benzenesulfonamido, N-methyltetradecylsulfonamido, and hexadecylsulfonamido; sulfamoyl, such as N-methylsulfamoyl, N-hexadecylsulfamoyl, N, N-dimethylsulfamoyl; N-[3-(dodecyloxy)propyl]sulfamoyl, N-[4-(2,4-di-t-pentylphenoxy)butyl]-sulfamoyl, N-methyl-N-tetradecylsulfamoyl, and N-dodecylsulfamoyl; sulfamido, such as N-methylsulfamido and N-octdecylsulfamido; sulfamido, such as methylsulfamido, phenylsulfamido, p-toluylsulfamido, p-dodecylphenylsulfamido, N-methyltetradecylsulfamido, and hexadecylsulfamido; carbamoyl, such as N-methylcarbamoyl, N-octadecylcarbamoyl, N-[4-(2,4-di-t-pentylphenoxy) butyl]carbamoyl, N-methyl-N-tetradecylcarbamoyl, and N,N-dioctyl-carbamoyl; diacylamino, such as N-succinimido, N-phthalimido, 2,5-dioxo-1-oxazolidinyl, 3-dodecyl-2,5-dioxo-1-imidazolyl, and N-acetyl-N-dodecylamino; aryloxycarbonyl, such as phenoxycarbonyl and p-dodecyl-oxyphenoxycarbonyl; alkoxycarbonyl, such as alkoxycarbonyl containing 2 to 30 carbon atoms, for example methoxycarbonyl, tetradecyloxycarbonyl, ethoxycarbonyl, benzyloxycarbonyl, and dodecyloxycarbonyl; alkoxysulfonyl, such as alkoxysulfonyl containing 1 to 30 carbon atoms, for example methoxysulfonyl, octyloxysulfonyl, tetradecyloxysulfonyl, and 2-ethylhexyloxysulfonyl; aryloxysulfonyl, such as phenoxysulfonyl, 2,4-di-t-pentylphenoxysulfonyl; alkylsulfonyl, such as alkylsulfonyl containing 1 to 30 carbon atoms, for example methylsulfonyl, octylsulfonyl, 2-ethylhexylsulfonyl, and hexadecylsulfonyl; arylsulfonyl, such as phenylsulfonyl, 4-nonylphenylsulfonyl, and p-toluylsulfonyl; alkylsulfinyl, such as alkylsulfinyl containing 1 to 30 carbon atoms, for example methylsulfinyl, octylsulfinyl, 2-ethylhexylsulfinyl,and hexadecylsulfinyl; arylsulfinyl, such as phenylsulfinyl, 4-nonylphenylsulfinyl, and p-toluylsulfinyl; alkylthio, such as alkylthio containing 1 to 22 carbon atoms, for example ethylthio, octylthio, benzylthio, tetradecylthio, and 2-(2,4-di-t-pentylphenoxy) ethylthio; arylthio, such as phenylthio and p-tolylthio; alkoxycarbonylamino, such as ethoxycarbonylamino, benzyloxycarbonylamino, and hexadecyloxycarbonylamino; aryloxycarbonylamino, such as phenylcarbonylamino, 2,5-(di-t-pentylphenyl) carbonylamino, and p-dodecylphenylcarbonylamino, and p-toluylcarbonylamino; alkylureido, such as N-methylureido, N, N-dimethylureido, N-methyl-N-dodecylureido, N-hexadecylureido, N, N-dioctadecylureido, and N, N-dioctyl-N'-ethyl-ureido; arylureido, such as N-phenylureido, N, N-diphenylureido, N-phenyl-N-p-toluylureido, N-(m-hexadecylphenyl)ureido, and N, N-(2,5-di-t-pentylphenyl)-N'-ethyl-ureido; acyloxy, such as acetyloxy, benzoyloxy, octadecanoyloxy, p-dodecylamidobenzoyloxy, and cyclohexylcarbonyloxy; nitro; carboxy (—COOH); and except for $G_1$, $G_2$, and $R_1$, hydrogen.

$G_3$ is suitably selected from hydrogen, halogen, acylamino, sulfonamido, sulfamido, carbamoyl, diacylamino, alkoxycarbonyl, aryloxycarbonyl, alkoxysulfonyl, aryloxysulfonyl, alkylsulfonyl, arylsulfonyl, alkylsulfinyl, arylsulfinyl, alkoxycarbonylamino, aryloxycarbonylamino, alkylureido, arylureido, acyloxy, trifluoromethyl and carboxyl with suitable specific examples of each group as specified above for $G_2$.

Among the compounds described above, a preferred embodiment is represented by the above formula wherein the substituents $X_1$, $X_2$, Y, $G_1$ and $G_2$ are individually selected from the group consisting of chloride, fluoride, acylamino, sulfonamido, sulfamoyl, carbamoyl, alkoxycarbonyl, aryloxycarbonyl, alkylsulfonyl, arylsulfonyl, alkoxycarbonylamino, aryloxycarbonylamino, alkylureido, arylureido, and trifluoromethyl.

A particularly preferred embodiment is represented by the above formula wherein the substituents $X_1$, $X_2$, and Y are chloride, $G_3$ is hydrogen, and $G_1$ and $G_2$ are individually selected from the group consisting of chloride, fluoride, acylamino, sulfonamido, sulfamoyl, carbamoyl, alkoxycarbonyl, aryloxycarbonyl, alkylsulfonyl, arylsulfonyl, alkoxycarbonylamino, aryloxycarbonylamino, alkylureido, arylureido, and trifluoromethyl.

Further, in the preferred embodiment, the substituent Z is a branched alkyl group containing at least three carbons and the total number of carbons in Z and $R_1$ sum to at least 6 carbons.

In a most preferred embodiment, substituents $X_1$, $X_2$, Y, and $G_1$ are chloride, "a" is equal to 1, $G_3$ is hydrogen, and $G_1$ is para to the pyrazolone ring, and $G_2$ is selected from the group consisting of chloride, fluoride, acylamino, sulfonamido, sulfamoyl, carbamoyl, alkoxycarbonyl, aryloxycarbonyl, alkylsulfonyl, arylsulfonyl, alkoxycarbonylamino, aryloxycarbonylamino, alkylureido, arylureido, and trifluoromethyl, provided that the sum of the Hammett's sigma values for $X_1$, $X_2$, Y, $G_1$ and $G_2$ is at least 1.3.

Higher minimum values for the sum of the Hammett's sigma values such as 1.4 and even 1.5 provide even better results than the lower values.

The term "coupler" herein refers to the entire compound, including the coupler moiety and the coupling-off group. The term "coupler moiety (COUP)" refers to that portion of the compound other than the coupling-off group.

The coupler moiety (COUP) can be any 3-anilinopyrazolone coupler moiety useful in the photographic art to form a color reaction product particularly a magenta dye, with oxidized color developing agent provided the substituents meet the requirements above described. Useful pyrazolone coupler moieties are described in, for example, U.S. Pat. Nos. 4,413,054; 4,853,319; 4,443,536; 4,199,361; 4,351,897; 4,385,111; Japanese Published Patent Application 60/170854; U.S. Pat. Nos. 3,419,391; 3,311,476; 3,519,429; 3,152,896; 2,311,082; and 2,343,703; the disclosures of which are incorporated herein by reference. The coupling-off group, if any, on the pyrazolone coupler moiety described in these patents or patent applications can be replaced by a coupling-off group according to the invention. The pyrazolone coupler according to the invention can be in a photographic element in combination with other magenta couplers known or used in the photographic art, such as in combination with at least one of the pyrazolone couplers described in these patents or published patent applications of the invention. The COUP portion of the couplers can be obtained as is known to the art. For example, syntheses of COUP moieties are described in Item 16736 in Research Disclosure, March 1978; U.K. Patent Specification 1,530,272; U.S. Pat. Nos. 3,907,571; and 3,928,044.

Illustrative couplers include:

A-1

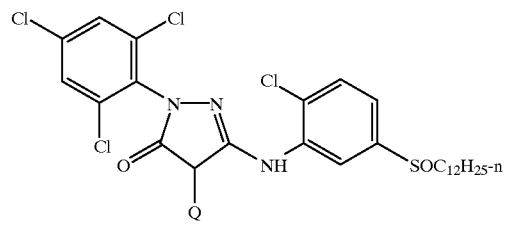

-continued
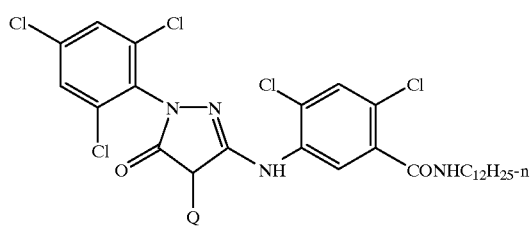
A-2
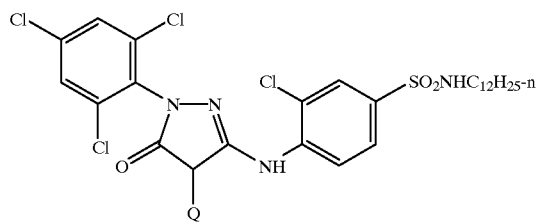
A-3
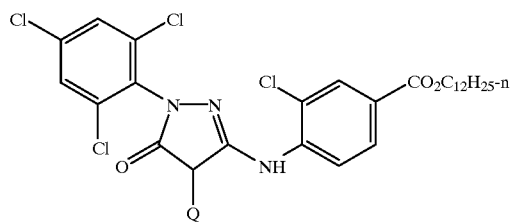
A-4
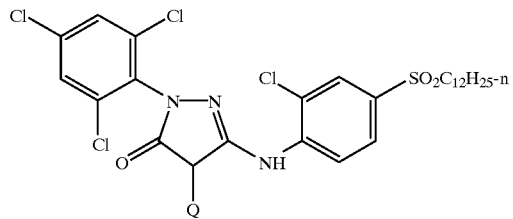
A-5
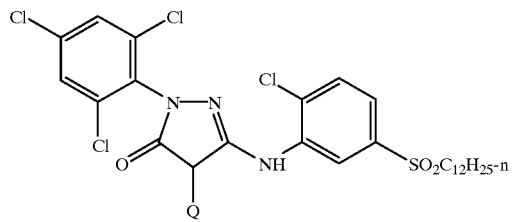
A-6
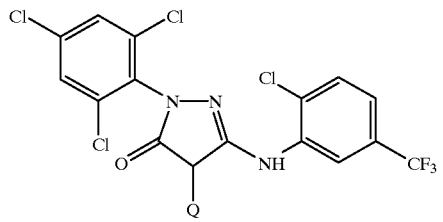
A-7

-continued
A-8
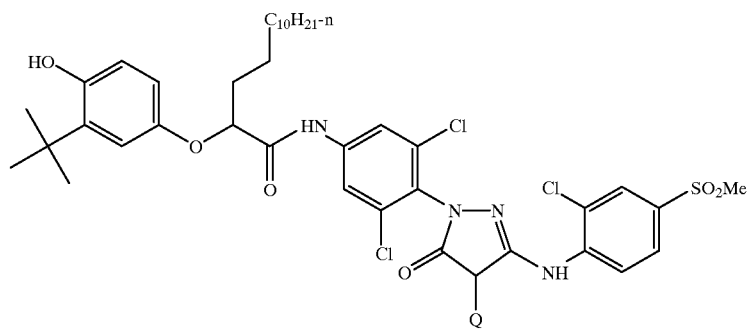
A-9
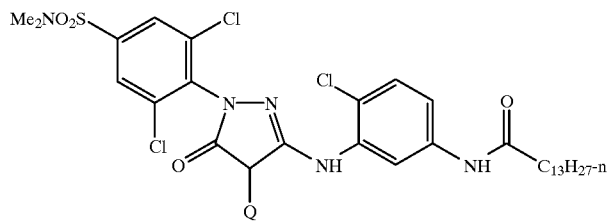
A-10
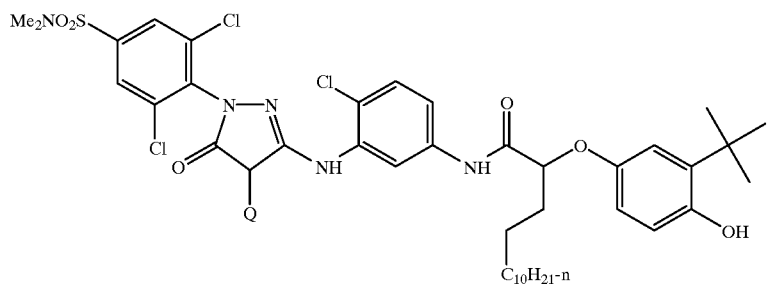
A-11
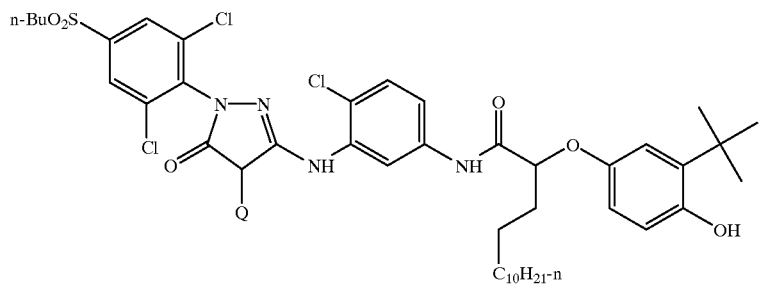
A-12
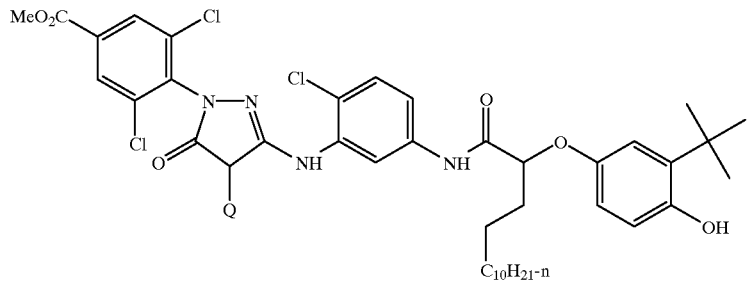

A-13

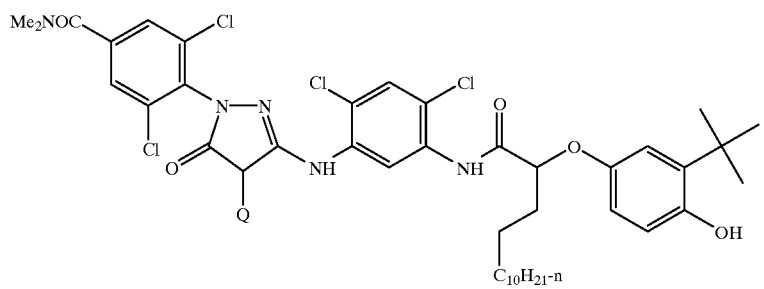

"Q" represents a coupling-off group according to the invention. Substituents that have been used or known on arylthio coupling-off groups on pyrazolone couplers can be used on Q. Optional substituents $R_1$ on this ring include the following: hydroxyl, halogen, alkyl, alkoxy, aryloxy, acylamino, alkylthio, arylthio, sulfonamido, sulfamoyl, sulfamido, carbamoyl, diacylamino, alkoxycarbonyl, aryloxycarbonyl, alkoxysulfonyl, aryloxysulfonyl, alkylsulfonyl, arylsulfonyl, alkylsulfinyl, arylsulfinyl, alkoxycarbonylamino, aryloxycarbonylamino, alkylureido, arylureido, acyloxy, nitro, trifluoromethyl and carboxy. Examples of these substituents are as specified above for $G_1$.

Illustrative coupling-off groups (Q) are as follows:

Q-1
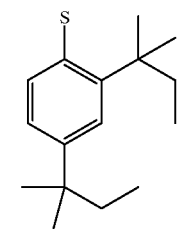

Q-2
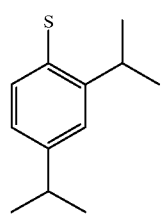

Q-3
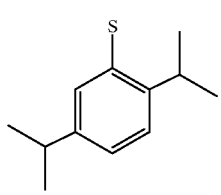

Q-4
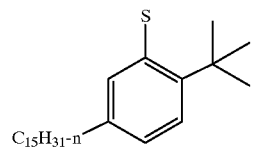

Q-5
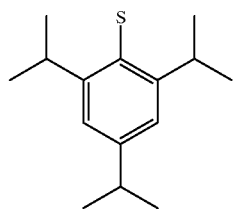

Q-6
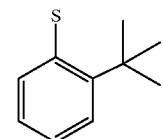

Q-7
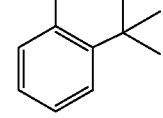

Q-8
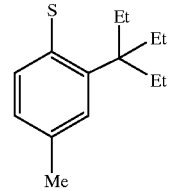

Q-9
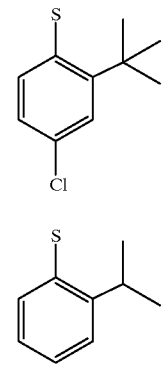

-continued

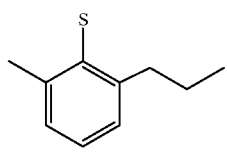
Q-10

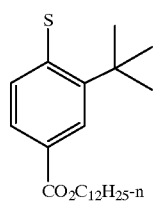
Q-11

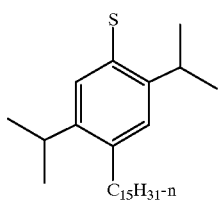
Q-12

Q-13

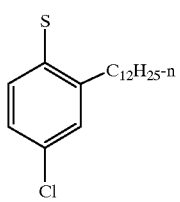
Q-14

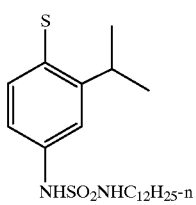
Q-15

The pyrazolone couplers preferably comprise a ballast group. The ballast group can be any ballast known in the photographic art and typically has from 6 to 30 carbon atoms. The ballast is typically one that does not adversely affect reactivity, stability and other desired properties of the coupler of the invention and does not adversely affect the stability, hue and other desired properties of the dye formed from the coupler. Illustrative useful ballast groups are described in the following examples.

Couplers of this invention can be prepared by reacting the parent 4-equivalent coupler containing no coupling-off group with the arylthiol of the coupling-off group according to the invention. This is a simple method and does not involve multiple complicated synthesis steps. The reaction is typically carried out in a solvent, such as dimethylformamide or pyridine.

The couplers according to the invention can be prepared by the following illustrative synthetic scheme, where COUP represents the coupler moiety having the coupling-off group attached at its coupling position:

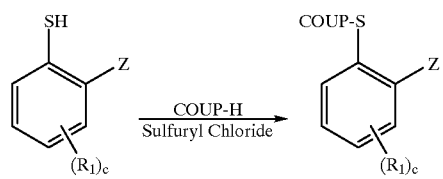

wherein COUP is the coupler moiety and Z and $R_1$ are as defined.

The following examples illustrate the preparation of couplers of this invention.

SYNTHESIS EXAMPLE A

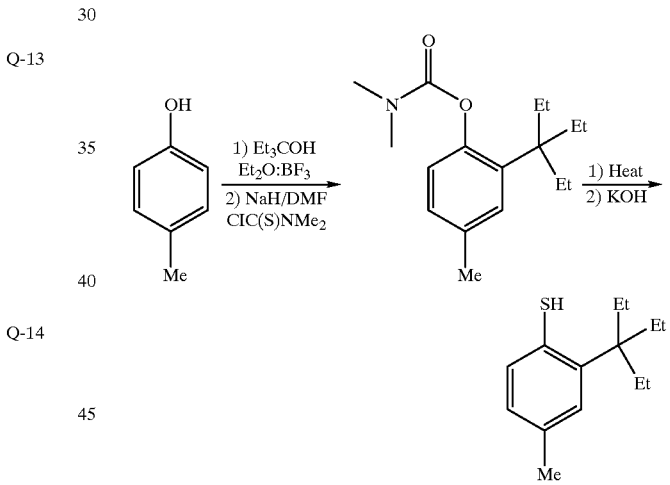

Synthesis of Leaving Groups, Synthesis of 2-tert-Heptyl-4-methylphenol: The multi-step synthetic sequence described for the synthesis of 2-t-heptyl-4-methylbenzenethiol is representative. An oven-dried 1-L flask fitted with a magnetic stirring bar and a pressure-equalizing dropping funnel was charged with 54 g (500 mmol) of p-cresol and 3-ethyl-3-pentanol 87.2 g (750 mmol). The flask was immersed in a water bath (~25° C.) and the mixture stirred well. Borontrifluoride-etherate 106.5 g (750 mmol) was added dropwise through the addition funnel over a period of 50 min. The reaction was monitored by TLC ($CH_2Cl_2$:EtOAc, 15:1) for the disappearance of p-cresol (2.5 h). Then, 250 mL of water was added and the contents heated to reflux to decompose excess $BF_3$:etherate complex. The mixture was cooled and extracted with ether (3×200 mL). The combined organic extracts were washed with brine and dried over $MgSO_4$. Removal of solvents on a rotary evaporator yielded a red/brown oil 118.9 g. This was further purified by flash chromatography (CH$_2$Cl$_2$:EtOAc, 20:1) to give 2-tert-heptyl-4-methylphenol 77.7 g (76%) as a pale yellow oil. $^1$H NMR (ppm): 0.7 [t, 9H, —[CH$_2$CH$_3$)$_3$], 1.85 [s, 6H, —[CH$_2$CH$_3$)$_3$], 2.25 (s, 3H, Ar—Me), 4.67 (s, 1H, —OH), 6.45–7.03 (3H, aromatic).

Synthesis of 2-tert-Heptyl-4-methylphenyl N,N-dimethyl-O-thiocarbamate: An oven-dried 1-L flask was fitted with a magnetic stirring bar and a pressure-equalizing dropping funnel connected to a mineral oil bubbler and was cooled under a stream of dry argon. The flask was charged with 17.5 g (365 mmol) of 50% sodium hydride dispersed in mineral oil and 150 mL of DMF. To this, well-stirred slurry maintained at 25° C. (water bath), 60 g (291 mmol) of 2-tert-heptyl-4-methylphenol dissolved in 150 mL of DMF was added dropwise (1 hr). The mixture was stirred for an additional period of 2.5 hr to complete the formation of the anion. N,N-Dimethylthiocarbamoylchloride 39.5 g (319 mmol) dissolved in 100 mL of DMF was added dropwise to the reaction mixture and monitored by TLC (ligroin 950:EtOAc 5:1). After 1 hr, the mixture was hydrolyzed with dropwise addition of water (35 mL) under argon followed by acidification (100 mL of 2M HCl). The mixture was extracted with 3×200 mL portions of ether. Removal of solvents after drying yielded 85 g (100%) of a red oil which on flash chromatography (ligroin 950:EtOAc 6:1) yielded 64 g (75%) of the titled product. $^1$H NMR, ppm: 0.72 [t, 9H, C(CH$_2$CH$_3$)$_3$], 1.75 [B, 6H, —CH$_2$CH$_3$×3], 2.35 (s, 3H, Ar—Me), 3.35 and 3.42 (s, 6H, —NMe$_2$), 6.9–7.15 (3H, aromatic).

Thermal Rearrangement of 2-t-Heptyl-4-Methylphenyl N,N-Dimethyl-O-thiocarbamate: A 500-mL flask equipped with a magnetic stirring bar and a reflux condenser connected to a mineral oil bubbler was charged with 57.6 g (196 mmol) of 2-t-heptyl-4-methylphenyl N,N-dimethylthiocarbamate. The flask was placed over a preheated heating mantle (~250° C.) and stirred well (25 min). The heating was removed and the contents were allowed to cool. TLC (ligroin 950:EtOAc 5:1) indicated the completion of reaction with some hydrolysis of the rearranged product to free thiol. It was directly used in the next step without further purification.

Hydrolysis of 2-t-Heptyl-4-Methylphenylthio-N N-dimethylcarbamate to 2-t-Heptyl-4-Methylbenzenethiol (Q-7): To the reaction mixture obtained in the previous reaction was added 110 mL of THF and 24.8 g (440 mmol) of potassium hydroxide dissolved in 100 mL of methanol. The mixture was stirred for 1.5 hr at 25° C. followed by heating at gentle reflux for 5 hr (completion of hydrolysis). The mixture was poured into crushed ice containing hydrochloric acid and extracted with 3×100 mmol portions of ether, washed with brine and dried (MgSO$_4$). Removal of solvent yielded a brown oil which on flash chromatography yielded 38.7 g (89%) of 2-t-heptyl-4-methylbenzenethiol (Q-7). This was found to be essentially pure and further purified by distillation, bp 95° C. (0.2 mm) to give a clear liquid. $^1$H NMR, ppm: 0.72 [t, 9H, —(CH$_2$CH$_3$)$_3$], 1.95 [q, 6H, —(CH$_2$CH$_3$)$_3$], 2.3 (s, 3H, Ar—CH$_3$), 3.54 (s, 1H, —SR). 6.8–7.2 (3H, aromatic). Anal. calcd. for C$_{14}$H$_{22}$S: C, 75–61; H, 9.97; S, 14.42. Found: C, 75.5; H, 9.9; S, 14.2.

Synthesis Example B: Synthesis of Coupler M-4.

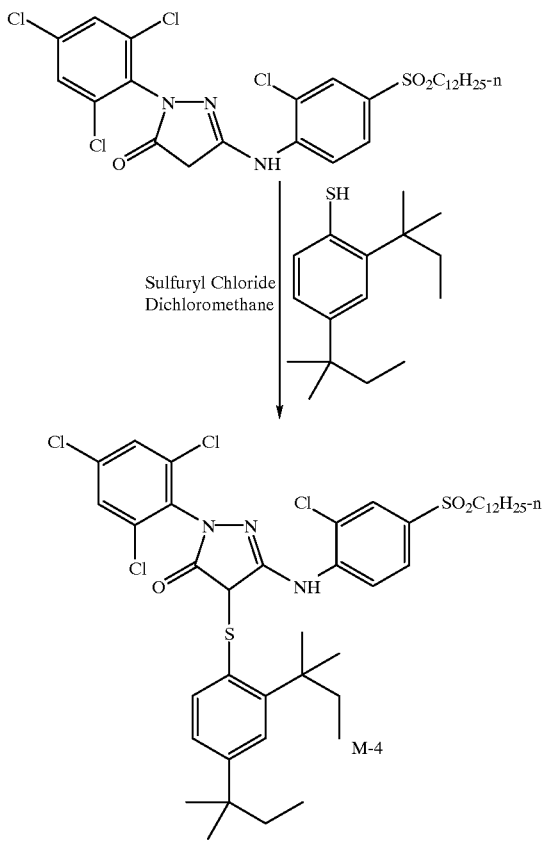

Synthesis of ArSCl: Sulfuryl chloride (2.6 g, 19 mmol) was slowly added to a solution of 2,4-di-tert-pentylbenzenethiol (7.51 g, 30 mmol) in dichloromethane (20 mL). After stirring at room temperature for 2 hrs, the volatiles were removed by rotary evaporation below 40° C.

Synthesis of Coupler: A solution of A-5 (Q=H, 11.2 g, 18 mmol) in DMF (50 mL) was added rapidly to the oil obtained above and the resulting solution was stirred at room temperature for 65 hr. The mixture was poured slowly into 3 N HCl (500 mL) and the precipitate was collected by suction filtration. The solid was dissolved in glacial acetic acid (350 mL) and reprecipitated into water. The resulting solid was collected filtration, washed well with water and air dried to give 10.0 g (64%) of M-4 as a white solid. $^1$H NMR was consistent with the structure; Anal. calcd. for C$_{43}$H$_{57}$Cl$_4$N$_3$O$_3$S$_2$: C, 59.4; H, 6.6; N, 4.8; Cl, 16.3; S, 7.4. Found: C, 58.2; H, 6.5; N, 4.8; Cl 16.1; S, 7.0.

The purity of the two-equivalent couplers synthesized was checked by (a) TLC in two or three different solvent systems of different polarity, (b) HPLC, (c) 270 MHz FT-NMR and (d) elemental analyses (C, H, N, Cl, S); some samples were also subjected to mass spectral analysis.

The following structures are included for comparative purposes:

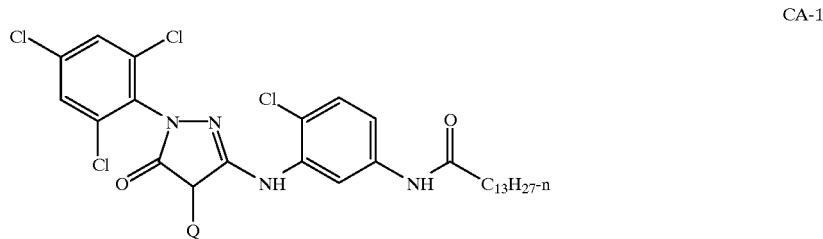
CA-1
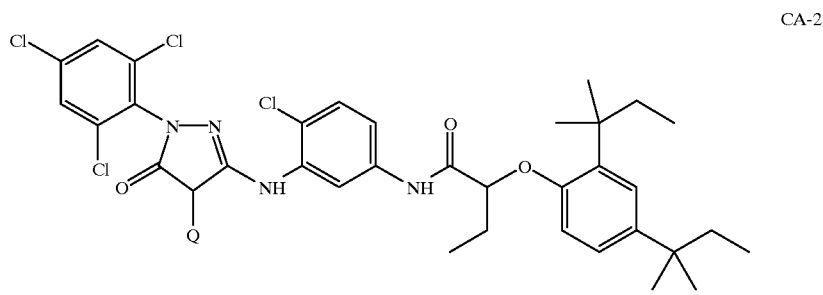
CA-2
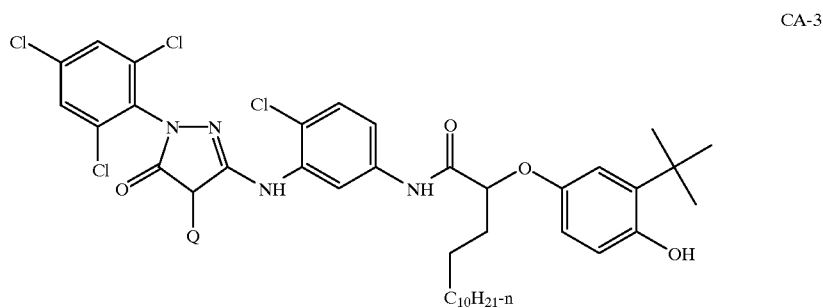
CA-3
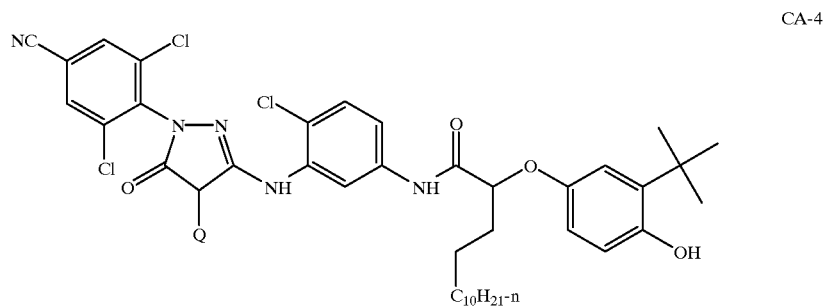
CA-4
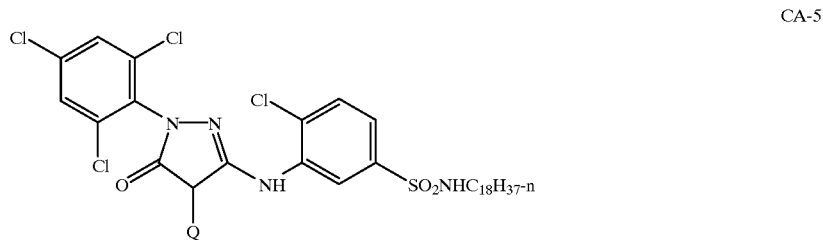
CA-5
CQ-1

-continued

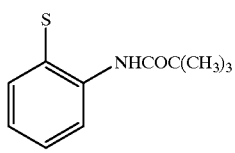

CQ-2

The following compounds were prepared by this general method:

TABLE I

Summary of Couplers

| Coupler (Type) | HPLC | | C | H | N | Cl | S | mp, °C. | COUP/Q |
|---|---|---|---|---|---|---|---|---|---|
| C-1 (Check) | na | calc. found | na | | | | | 165–167 | CA-1/CQ-1 |
| C-2 (Check) | na | calc. found | na | | | | | 129–133 | CA-1/CQ-2 |
| C-3 (Check) | 96 | calc. found | 62.6 62.2 | 7.0 6.8 | 6.5 6.5 | 3.7 3.7 | | 206–208 | CA-1/Q-1 |
| C-4 (Check) | 90 | calc. found | 65.6 65.4 | 7.9 7.7 | 5.7 5.6 | 14.3 14.0 | 3.2 3.1 | 174–176 | CA-1/Q-4 |
| C-5 (Check) | na | calc. found | 61.9 61.2 | 6.8 6.7 | 6.7 6.7 | 17.0 17.2 | 3.8 4.0 | 230–232 | CA-1/Q-7 |
| C-6 (Check) | >90 | calc. found | 64.1 63.9 | 6.8 6.8 | 5.9 5.9 | 14.8 14.4 | 3.4 3.2 | 131–134 | CA-2/Q-1 |
| C-7 (Check) | 97 | calc. found | 62.8 62.9 | 6.2 6.4 | 6.2 6.3 | 15.8 15.1 | 3.6 3.2 | 223–223 | CA-2/Q-3 |
| C-8 (Check) | 98 | calc. found | 63.1 62.8 | 6.6 6.5 | 5.8 5.6 | 14.6 14.4 | 3.3 3.5 | 172 | CA-3/Q-2 |
| C-9 (Check) | 96 | calc. found | 61.0 60.9 | 6.5 6.5 | 6.9 6.9 | 17.6 17.6 | 4.0 4.1 | 169–171 | CA-1/Q-3 |
| C-10 (check) | 98 | calc. found | 60.7 60.7 | 7.3 7.2 | 5.8 5.7 | 14.6 14.6 | 6.4 6.4 | 155–157 | CA-5/Q-1 |
| M-1 (Inven.) | 91 | calc. found | 58.4 58.5 | 6.6 6.5 | 6.3 6.2 | 16.0 16.0 | 7.2 6.9 | 71–75 | A-3/Q-1 |
| M-2 (Inven.) | 96 | calc. found | 56.5 56.4 | 6.1 6.1 | 6.8 6.7 | 17.1 17.3 | 7.7 7.6 | 69–75 | A-3/Q-3 |
| M-3 (Inven.) | 97 | calc. found | 57.5 57.6 | 6.3 6.1 | 6.5 6.3 | 16.5 16.2 | 7.5 decomp 7.2 | | A-3/Q-7 |
| M-4 (Inven.) | 99 | calc. found | 59.4 58.2 | 6.6 6.5 | 4.8 4.8 | 16.3 16.1 | 7.4 7.0 | na | A-5/Q-1 |
| M-5 (Inven.) | 100 | calc. found | 57.6 57.4 | 6.1 6.1 | 5.2 5.1 | 17.4 17.3 | 7.9 7.5 | na | A-5/Q-2 |
| M-6 (Inven.) | 95 | calc. found | 57.6 57.4 | 6.1 6.1 | 5.2 5.1 | 17.4 16.5 | 7.9 7.6 | 88 | A-5/Q-3 |
| M-7 (Inven.) | 96 | calc. found | 60.3 60.1 | 6.1 7.0 | 7.5 7.3 | 11.4 10.8 | 6.8 6.6 | na | A-9/Q-1 |

Table I summarizes the comparison (C) and invention (M) couplers synthesized for testing. Table II summarizes the Hanmett's sigma values associated with the couplers. The values for Hamett's $sigma_{para}$ were used to estimate the value for substituents ortho to the pyrazolone nucleus.

TABLE II

Sigma Constant Values

| | Hammett's Sigma Values | | | | | | Sum of Hammett's |
|---|---|---|---|---|---|---|---|
| Coupler | $X_1$ | $X_2$ | Y | $G_1$ | $G_2$ | $G_3$ | Sigma Values |
| C-1 | 0.23 | 0.23 | 0.23 | 0.23 | 0.00 | 0.21 | 1.13 |
| C-2 | 0.23 | 0.23 | 0.23 | 0.23 | 0.00 | 0.21 | 1.13 |
| C-3 | 0.23 | 0.23 | 0.23 | 0.23 | 0.00 | 0.21 | 1.13 |
| C-4 | 0.23 | 0.23 | 0.23 | 0.23 | 0.00 | 0.21 | 1.13 |

TABLE II-continued

Sigma Constant Values

| | Hammett's Sigma Values | | | | | | Sum of Hammett's |
|---|---|---|---|---|---|---|---|
| Coupler | $X_1$ | $X_2$ | Y | $G_1$ | $G_2$ | $G_3$ | Sigma Values |
| C-5 | 0.23 | 0.23 | 0.23 | 0.23 | 0.00 | 0.21 | 1.13 |
| C-6 | 0.23 | 0.23 | 0.23 | 0.23 | 0.00 | 0.21 | 1.13 |
| C-7 | 0.23 | 0.23 | 0.23 | 0.23 | 0.00 | 0.21 | 1.13 |
| C-8 | 0.23 | 0.23 | 0.23 | 0.23 | 0.00 | 0.21 | 1.13 |
| C-9 | 0.23 | 0.23 | 0.23 | 0.23 | 0.00 | 0.21 | 1.13 |
| C-10 | 0.23 | 0.23 | 0.23 | 0.23 | 0.00 | 0.46 | 1.38 |
| M-1 | 0.23 | 0.23 | 0.23 | 0.23 | 0.57 | 0.00 | 1.49 |
| M-2 | 0.23 | 0.23 | 0.23 | 0.23 | 0.57 | 0.00 | 1.49 |
| M-3 | 0.23 | 0.23 | 0.23 | 0.23 | 0.57 | 0.00 | 1.49 |
| M-4 | 0.23 | 0.23 | 0.23 | 0.23 | 0.78 | 0.00 | 1.64 |
| M-5 | 0.23 | 0.23 | 0.23 | 0.23 | 0.78 | 0.00 | 1.64 |
| M-6 | 0.23 | 0.23 | 0.23 | 0.23 | 0.78 | 0.00 | 1.64 |
| M-7 | 0.23 | 0.23 | 0.23 | 0.57 | 0.00 | 0.21 | 1.47 |

The couplers of this invention can be used in the ways and for the purposes that couplers are used in the photographic art.

Typically, the coupler is incorporated in a silver halide emulsion and the emulsion coated on a support to form part of a photographic element. Alternatively, the coupler can be incorporated at a location adjacent to the silver halide emulsion where, during development, the coupler will be in reactive association with development products such as oxidized color developing agent. Thus, as used herein, the term "associated therewith" signifies that the coupler is in the silver halide emulsion layer or in an adjacent location where, during processing, the coupler is capable of reacting with silver halide development products.

The photographic elements can be single color elements or multicolor elements. Multicolor elements contain dye image-forming units sensitive to each of the three primary regions of the spectrum. Each unit can be comprised of a single emulsion layer or of multiple emulsion layers sensitive to a given region of the spectrum. The layers of the element, including the layers of the image-forming units, can be arranged in various orders as known in the art. In an alternative format, the emulsions sensitive to each of the three primary regions of the spectrum can be disposed as a single segmented layer.

A typical multicolor photographic element comprises a support bearing a cyan dye image-forming unit comprised of at least one red-sensitive silver halide emulsion layer having associated therewith at least one cyan dye-forming coupler, a magenta dye image-forming unit comprising at least one green-sensitive silver halide emulsion layer having associated therewith at least one magenta dye-forming coupler, and a yellow dye image-forming unit comprising at least one blue-sensitive silver halide emulsion layer having associated therewith at least one yellow dye-forming coupler, at least one of the couplers in the element being a coupler of this invention. The element can contain additional layers, such as filter layers, interlayers, overcoat layers, subbing layers, and the like.

In the following discussion of suitable materials for use in the emulsions and elements of this invention, reference will be made to *Research Disclosure,* December 1989, Item 308119, published by Kenneth Mason Publications, Ltd., Dudley Annex, 12a North Street, Emsworth, Hampshire P010 7DQ, ENGLAND, which will be identified hereafter by the term "Research Disclosure." The contents of the Research Disclosure, including the patents and publications referenced therein, are incorporated herein by reference, and the Sections hereafter referred to are Sections of the Research Disclosure.

The silver halide emulsions employed in the elements of this invention can be either negative-working or positive-working. Suitable emulsions and their preparation as well as methods of chemical and spectral sensitization are described in Sections I through IV. Color materials and development modifiers are described in Sections V and XXI. Vehicles are described in Section IX, and various additives such as brighteners, antifoggants, stabilizers, light absorbing and scattering materials, hardeners, coating aids, plasticizers, lubricants and matting agents are described, for example, in Sections V, VI, VIII, X, XI, XII, and XVI. Manufacturing methods are described in Sections XIV and XV, other layers and supports in Sections XIII and XVII, processing methods and agents in Sections XIX and XX, and exposure alternatives in Section XVIII.

Preferred color developing agents are p-phenylene diamines. Especially preferred are:
4-amino-N,N-diethylaniline hydrochloride,
4-amino-3-methyl-N,N-diethylaniline hydrochloride,
4-amino-3-methyl-N-ethyl-N-(β-(methanesulfonamido) ethyl) aniline sesquisulfate hydrate,
4-amino-3-methyl-N-ethyl-N-(β-hydroxyethyl)aniline sulfate,
4-amino-3-β-(methanesulfonamido)ethyl-N,N-diethylaniline hydrochloride and
4-amino-N-ethyl-N-(2-methoxyethyl)-m-toluidine di-p-toluene sulfonic acid.

With negative working silver halide a negative image can be formed. Optionally positive (or reversal) image can be formed.

The magenta coupler described herein may be used in combination with other classes of magenta image couplers such as 3-acylamino-5-pyrazolones and heterocyclic couplers (e.g. pyrazoloazoles) such as those described in EP 285,274; U.S. Pat. No. 4,540,654; EP 119,860, or with other 5-pyrazolone couplers containing different ballasts or coupling-off groups such as those described in U.S. Pat. Nos. 4,301,235; 4,853,319 and 4,351,897. The coupler may also be used in association with yellow or cyan colored couplers (e.g. to adjust levels of interlayer correction) and with masking couplers such as those described in EP 213, 490; Japanese Published Application 58-172,647; U.S. Pat. No. 2,983,608; German Application DE 2,706,117C; U.K. Patent 1,530,272; Japanese Application A-113935; U.S. Pat. No. 4,070,191 and German Application DE 2,643,965. The masking couplers may be shifted or blocked.

The coupler may also be used in association with materials that accelerate or otherwise modify the processing steps e.g. of bleaching or fixing to improve the quality of the image. Bleach accelerators described in EP 193,389; EP 301,477; U.S. Pat. Nos. 4,163,669; 4,865,956; and 4,923, 784 are particularly useful. Also contemplated is use of the coupler in association with nucleating agents, development accelerators or their precursors (UK Patent 2,097,140; U.K. Patent 2,131,188); electron transfer agents (U.S. Pat. Nos. 4,859,578; 4,912,025); antifogging and anti color-mixing agents such as derivatives of hydroquinones, aminophenols, amines, gallic acid; catechol; ascorbic acid; hydrazides; sulfonamidophenols; and non color-forming couplers. Suitable hydroquinone color fog inhibitors include, but are not limited to compounds disclosed in EP 69,070; EP 98,241; EP 265,808; Japanese Published Patent Applications 61/233, 744; 62/178,250; and 62/178,257. In addition, specifically contemplated are 1,4-benzenedipentanoic acid, 2,5-dihydroxy-Δ,Δ,Δ',Δ'-tetramethyl-, dihexyl ester; 1,4-Benzenedipentanoic acid, 2-hydroxy-5-methoxy-Δ,Δ,Δ',Δ'-tetramethyl-, dihexyl ester; and 2,5-dimethoxy-Δ,Δ,Δ',Δ'-tetramethyl-, dihexyl ester. In addition, it is contemplated that materials of this invention may be used with so called liquid ultraviolet absorbers such as described in U.S. Pat. Nos. 4,992,358; 4,975,360; and 4,587,346.

Various kinds of discoloration inhibitors can be used with materials of this invention. Typical examples of organic discoloration inhibitors include hindered phenols represented by hydroquinones, 6-hydroxychromans, 5-hydroxycoumarans, spirochromans, p-alkoxyphenols and bisphenols, gallic acid derivatives, methylenedioxybenzenes, aminophenols, hindered amines, and ether or ester derivatives obtained by silylation, alkylation or acylation of phenolic hydroxy groups of the above compounds. Also, metal complex salts represented by (bis-salicylaldoximato)nickel complex and (bis-N,N-dialkyldithiocarbamato)nickel complex can be employed as a discoloration inhibitor. Specific examples of the organic discoloration inhibitors are described below. For instance, those of hydroquinones are disclosed in U.S. Pat. Nos. 2,360,290; 2,418,613; 2,700,453; 2,701,197; 2,710,801; 2,816,028; 2,728,659; 2,732,300; 2,735,765; 3,982,944 and 4,430,425; and British Patent 1,363,921; and so on; 6-hydroxychromans, 5-hydroxycoumarans, spirochromans are disclosed in U.S. Pat. Nos. 3,432,300; 3,573,050; 3,574, 627; 3,698,909 and 3,764,337; and Japanese Published Patent Application 52-152,225; and so on; spiroindanes are disclosed in U.S. Pat. No. 4,360,589; those of p-alkoxyphenols are disclosed in U.S. Pat. No. 2,735,765; British Patent 2,066,975; Japanese Published Patent Applications 59-010,539 and 57-019,765; and so on; hindered phenols are disclosed, for example, in U.S. Pat. No. 3,700, 455; 4,228,235; Japanese Published Patent Applications 52-072,224 and 52-006,623; and so on; gallic acid derivatives, methylenedioxybenzenes and aminophenols are disclosed in U.S. Pat. Nos. 3,457,079; 4,332,886; and Japanese Published Patent Application 56-021,144, respectively; hindered amines are disclosed in U.S. Pat. Nos. 3.336,135; 4,268,593; British Patents 1,326,889; 1,354,313 and 1,410, 846; Japanese Published Patent Applications 51-001,420; 58-114,036; 59-053,846; 59-078,344; and so on; those of ether or ester derivatives of phenolic hydroxy groups are disclosed in U.S. Pat. Nos. 4,155,765; 4,174,220; 4,254,216; 4,279,990; Japanese Published Patent Applications 54-145, 530; 55-006,321; 58-105,147; 59-010,539; 57-037,856; 53-003,263 and so on; and those of metal complexes are disclosed in U.S. Pat. Nos. 4,050,938 and 4,241,155.

Any addenda conventionally employed in conjunction with magenta couplers such as amine stabilizers (e.g. those described in U.S. Pat. No. 5,096,805) are suitably used with these couplers.

For example, the coupler of the invention may be used to replace all or part of the image coupler or may be added to one or more of the other layers in a color negative photographic element comprising a support bearing the following layers from top to bottom:

(1) one or more overcoat layers containing ultraviolet absorber(s);

(2) a two-coat yellow pack with a fast yellow layer containing "Coupler 1": Benzoic acid, 4-chloro-3-((2-(4-ethoxy-2,5-dioxo-3-(phenylmethyl)-1-imidazolidinyl)-3-(4-methoxyphenyl)-1,3-dioxopropyl)amino)-, dodecyl ester and a slow yellow layer containing the same compound together with "Coupler 2": Propanoic acid, 2-[[5-[[4-[2-[[[2,4-bis(1,1-dimethylpropyl)phenoxy]acetyl]amino]-5-[(2,2,3,3,4,4,4-heptafluoro-1-oxobutyl)amino]-4-hydroxyphenoxy]-2,3-dihydroxy-6-[(propylamino) carbonyl ]phenyl]thio]-1,3,4-thiadiazol-2-yl]thio]-, methyl ester and "Coupler 3": 1-((dodecyloxy) carbonyl) ethyl(3-chloro-4-((3-(2-chloro-4-((1-tridecanoylethoxy) carbonyl)anilino)-3-oxo-2-((4)(5)(6)-(phenoxycarbonyl)-1H-benzotriazol-1-yl) propanoyl)amino))benzoate;

(3) an interlayer containing fine metallic silver;

(4) a triple-coat magenta pack with a fast magenta layer containing "Coupler 4": Benzamide, 3-((2-(2,4-bis(1,1-dimethylpropyl)phenoxy)-1-oxobutyl)amino)-N-(4,5-dihydro-5-oxo-1-(2,4,6-trichlorophenyl)-1H-pyrazol-3-yl)-, "Coupler 5": Benzamide, 3-((2-(2,4-bis(1,1-dimethylpropyl)phenoxy)-1-oxobutyl)amino)-N-(4',5'-dihydro-5'-oxo-1'-(2,4,6-trichlorophenyl) (1,4'-bi-1H-pyrazol)-3'-yl)-, "Coupler 6": Carbamic acid, (6-(((3-(dodecyloxy)propyl) amino)carbonyl)-5-hydroxy-1-naphthalenyl)-, 2-methylpropyl ester, "Coupler 7": Acetic acid, ((2-((3-(((3-(dodecyloxy)propyl) amino) carbonyl)-4-hydroxy-8-(((2-methylpropoxy) carbonyl) amino)-1-naphthalenyl)oxy )ethyl)thio]-, and "Coupler 8" Benzamide, 3-((2-(2,4-bis(1,1-dimethylpropyl) phenoxy)-1-oxobutyl)amino)-N-(4,5-dihydro-4-((4-methoxyphenyl) azo)-5-oxo-1-(2,4,6-trichlorophenyl)-1H-pyrazol-3-yl)-; a mid-magenta layer and a slow magenta layer each containing "Coupler 9": a ternary copolymer containing by weight in the ratio 1:1:2 2-Propenoic acid butyl ester, styrene, and N-[1-(2,4,6-trichlorophenyl)-4,5-dihydro-5-oxo-1H-pyrazol-3-yl]-2-methyl-2-propenamide; and "Coupler 10": Tetradecanamide, N-(4-chloro-3-((4-((4-((2,2-dimethyl-1-oxopropyl) amino)phenyl)azo)-4,5-dihydro-5-oxo-1-(2,4,6-trichlorophenyl)-1H-pyrazol-3-yl)amino)phenyl)-, in addition to Couplers 3 and 8;

(5) an interlayer;

(6) a triple-coat cyan pack with a fast cyan layer containing Couplers 6 and 7; a mid-cyan containing Coupler 6 and "Coupler 11": 2,7-Naphthalenedisulfonic acid, 5-(acetylamino)-3-((4-(2-((3-(((3-(2,4-bis(1,1-dimethylpropyl)phenoxy) propyl)amino)carbonyl)-4-hydroxy-1-naphthalenyl) oxy)ethoxy)phenyl)azo)-4-hydroxy-, disodium salt; and a slow cyan layer containing Couplers 2 and 6;

(7) an undercoat layer containing Coupler 8; and (8) an antihalation layer.

In a color paper format, the coupler of the invention may suitably be used to replace all or a part of the image coupler or added to a layer in a photographic element such as one comprising a support bearing the following from top to bottom:

(1) one or more overcoats;

(2) a cyan layer containing "Coupler 1": Butanamide, 2-(2,4-bis(1,1-dimethylpropyl)phenoxy)-N-(3,5-dichloro-2-hydroxy-4-methylphenyl)-, "Coupler 2": Acetamide, 2-(2,4-bis(1,1-dimethylpropyl)phenoxy)-N-(3,5-dichloro-2-hydroxy-4-, and UV Stabilizers: Phenol, 2-(5-chloro-2H-benzotriazol-2-yl)-4,6-bis(1,1-dimethylethyl)-; Phenol, 2-(2H-benzotriazol-2-yl)-4-(1,1-dimethylethyl)-; Phenol, 2-(2H-benzotriazol-2-yl)-4-(1,1-dimethylethyl)-6-(1-methylpropyl)-; and Phenol, 2-(2H-benzotriazol-2-yl)-4,6-bis(1,1-dimethylpropyl)- and a poly(t-butylacrylamide) dye stabilizer;

(3) an interlayer;

(4) a magenta layer containing "Coupler 3": Octanamide, 2-[2,4-bis(1,1-dimethylpropyl)phenoxy]-N-[2-(7-chloro-6-methyl-1H-pyrazolo[1,5-b][1,2,4]triazol-2-yl)propyl]- together with 1,1'-Spirobi(1H-indene), 2,2',3,3'-tetrahydro-3,3,3',3'-tetramethyl-5,5',6,6'-tetrapropoxy-;

(5) an interlayer; and (6) a yellow layer sontaining "Coupler 4": 1-Imidazolidineacetamide, N-(5-((2-(2,4-bis(1,1-dimethylpropyl)phenoxy)-1-oxobutyl)amino)-2-chlorophenyl)-α-(2,2-dimethyl-1-oxopropyl)-4-ethoxy-2,5-dioxo-3-(phenylmethyl)-.

In a reversal medium, the coupler of the invention could be used to replace all or part of the image coupler or added to a layer in a photographic element such as one comprising a support and bearing the following layers from top to bottom:

(1) one or more overcoat layers;

(2) a nonsensitized silver halide containing layer;

(3) a triple-coat yellow layer pack with a fast yellow layer containing "Coupler 1": Benzoic acid, 4-(1-(((2-chloro-5-((dodecylsulfonyl)amino)phenyl) amino) carbonyl)-3,3-dimethyl-2-oxobutoxy)-, 1-methylethyl ester; a mid yellow layer containing Coupler 1 and "Coupler 2": Benzoic acid, 4-chloro-3-[[2-[4-ethoxy-2,5-dioxo-3-(phenylmethyl)-1-imidazolidinyl]-4,4-dimethyl-1,3-dioxopentyl]amino]-, dodecylester; and a slow yellow layer also containing Coupler 2;

(4) an interlayer;

(5) a layer of fine-grained silver;

(6) an interlayer;

(7) a triple-coated magenta pack with a fast magenta layer containing "Coupler 3": 2-Propenoic acid, butyl ester, polymer with N-[1-(2,5-dichlorophenyl)-4,5-dihydro-5-oxo-1H-pyrazol-3-yl]-2-methyl-2-propenamide; "Coupler 4": Benzamide, 3-((2-(2,4-bis(1,1-dimethylpropyl)phenoxy)-1-oxobutyl)amino)-N-(4,5-dihydro-5-oxo-1-(2,4,6-trichlorophenyl)-1H-pyrazol-3-yl)-; and "Coupler 5": Benzamide, 3-(((2,4-bis(1,1-dimethylpropyl)phenoxy)acetyl)amino)-N-(4,5-dihydro-5-oxo-1-(2,4,6-trichlorophenyl)-1H-pyrazol-3-yl)-; and containing the stabilizer 1,1'-Spirobi(1H-indene), 2,2',3,3'-tetrahydro-3,3,3',3'-tetramethyl-5,5', 6,6'-tetrapropoxy-; and in the slow magenta layer Couplers 4 and 5 with the same stabilizer;

(8) one or more interlayers possibly including fine-grained nonsensitized silver halide;

(9) a triple-coated cyan pack with a fast cyan layer containing "Coupler 6": Tetradecanamide, 2-(2-cyanophenoxy)-N-(4-((2,2,3,3,4,4,4-heptafluoro-1-oxobutyl)amino)-3-hydroxyphenyl)-; a mid cyan containing "Coupler 7": Butanamide, N-(4-((2-(2,4-bis(1,1-dimethylpropyl)phenoxy)-1-oxobutyl)amino)-2-hydroxyphenyl)-2,2,3,3,4,4,4-heptafluoro- and "Coupler 8": Hexanamide, 2-(2,4-bis(1,1-dimethylpropyl)phenoxy)-N-(4-((2,2,3,3,4,4,4-heptafluoro-1-oxobutyl)amino)-3-hydroxyphenyl)-;

(10) one or more interlayers possibly including fine-grained nonsensitized silver halide; and

(11) an antihalation layer.

The couplers of the invention are useful with gelatin hardeners known to the art, such as bis(vinylsulfonyl)methane, bis(vinylsulfonyl)methyl ether, 1,2-bis(vinylsulfonyl-acetamido)ethane, 2,4-dichloro-6-hydroxy-s-triazine, triacryloyltriazine, and pyridinium, 1-(4-morpholinylcarbonyl)-4-(2-sulfoethyl)hydroxide, inner salt. Further, it is contemplated that the couplers of the invention would be particularly useful with so-called rapid acting hardeners, such as described in U.S. Pat. Nos. 4,418,142; 4,618,873; 4,673,632; 4,863,841; 4,877,724; 5,009,990; and 5,236,822.

The couplers may also be used in combination with filter dye layers comprising colloidal silver sol or yellow and/or magenta filter dyes, either as oil-in-water dispersions, latex dispersions or as solid particle dispersions. Additionally, they may be used with "smearing" couplers (e.g. as described in U.S. Pat. No. 4,366,237; EP 96,570; U.S. Pat. Nos. 4,420,556; and 4,543,323). Also, the couplers may be blocked or coated in protected form as described, for example, in Japanese Application 61/258,249 or U.S. Pat. No. 5,019,492.

The coupler may further be used in combination with image-modifying compounds such as "Developer Inhibitor-Releasing" compounds (DIR's). DIR's useful in conjunction with the couplers of the invention are known in the art and examples are described in U.S. Pat. Nos. 3,137,578; 3,148,022; 3,148,062; 3,227,554; 3,384,657; 3,379,529; 3,615,506; 3,617,291; 3,620,746; 3,701,783; 3,733,201; 4,049,455; 4,095,984; 4,126,459; 4,149,886; 4,150,228; 4,211,562; 4,248,962; 4,259,437; 4,362,878; 4,409,323; 4,477,563; 4,782,012; 4,962,018; 4,500,634; 4,579,816; 4,607,004; 4,618,571; 4,678,739; 4,746,600; 4,746,601; 4,791,049; 4,857,447; 4,865,959; 4,880,342; 4,886,736; 4,937,179; 4,946,767; 4,948,716; 4,952,485; 4,956,269; 4,959,299; 4,966,835; 4,985,336 as well as in patent publications GB 1,560,240; GB 2,007,662; GB 2,032,914; GB 2,099,167; DE 2,842,063, DE 2,937,127; DE 3,636,824; DE 3,644,416 as well as the following European Patent Publications: 272,573; 335,319; 336,411; 346, 899; 362, 870; 365,252; 365,346; 373,382; 376,212; 377,463; 378,236; 384,670; 396,486; 401,612; 401,613.

Such compounds are also disclosed in "Developer-Inhibitor-Releasing (DIR) Couplers for Color Photography," C. R. Barr, J. R. Thirtle and P. W. Vittum in *Photographic Science and Engineering*, Vol. 13, p. 174 (1969), incorporated herein by reference. Generally, the developer inhibitor-releasing (DIR) couplers include a coupler moiety and an inhibitor coupling-off moiety (IN). The inhibitor-releasing couplers may be of the time-delayed type (DIAR couplers) which also include a timing moiety or chemical switch which produces a delayed release of inhibitor. Examples of typical inhibitor moieties are: oxazoles, thiazoles, diazoles, triazoles, oxadiazoles, thiadiazoles, oxathiazoles, thiatriazoles, benzotriazoles, tetrazoles, benzimidazoles, indazoles, isoindazoles, mercaptotetrazoles, selenotetrazoles, mercaptobenzothiazoles, selenobenzothiazoles, mercaptobenzoxazoles, selenobenzoxazoles, mercaptobenzimidazoles, selenobenzimidazoles, benzodiazoles, mercaptooxazoles, mercaptothiadiazoles, mercaptothiazoles, mercaptotriazoles, mercaptooxadiazoles, mercaptodiazoles, mercaptooxathiazoles, telleurotetrazoles or benzisodiazoles. In a preferred embodiment, the inhibitor moiety or group is selected from the following formulas:

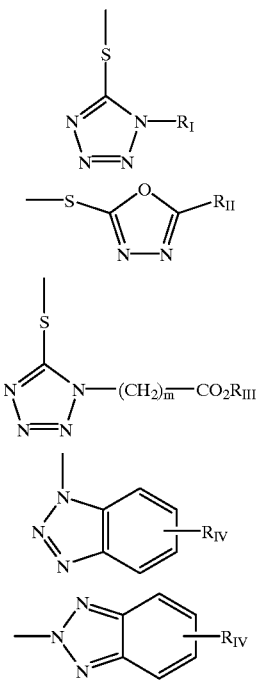

wherein $R_I$ is selected from the group consisting of straight and branched alkyls of from 1 to about 8 carbon atoms, benzyl and phenyl groups and said groups containing at least one alkoxy substituent; $R_{II}$ is selected from $R_I$ and —$SR_I$; $R_{III}$ is a straight or branched alkyl group of from 1 to about 5 carbon atoms and m is from 1 to 3; and $R_{IV}$ is selected from the group consisting of hydrogen, halogens and alkoxy, phenyl and carbonamido groups, —$COOR_V$ and —$NHCOOR_V$ wherein $R_V$ is selected from substituted and unsubstituted alkyl and aryl groups.

Although it is typical that the coupler moiety included in the developer inhibitor-releasing coupler forms an image dye corresponding to the layer in which it is located, it may also form a different color as one associated with a different film layer. It may also be useful that the coupler moiety included in the developer inhibitor-releasing coupler forms colorless products and/or products that wash out of the photographic material during processing (so-called "universal" couplers).

As mentioned, the developer inhibitor-releasing coupler may include a timing group which produces the time-delayed release of the inhibitor group such as groups utilizing the cleavage reaction of a hemiacetal (U.S. Pat. No. 4,146,396, Japanese Applications 60-249148; 60-249149); groups using an intramolecular nucleophilic substitution reaction (U.S. Pat. No. 4,248,962); groups utilizing an electron transfer reaction along a conjugated system (U.S. Pat. Nos. 4,409,323; 4,421,845; Japanese Applications 57-188035; 58-98728; 58-209736; 58-209738) groups utilizing ester hydrolysis (German Patent Application (OLS) No. 2,626,315); groups utilizing the cleavage of imino ketals (U.S. Pat. No. 4,546,073); groups that function as a coupler or reducing agent after the coupler reaction (U.S. Pat. Nos. 4,438,193; 4,618,571) and groups that combine the features describe above. It is typical that the timing group or moiety is of one of the formulas:

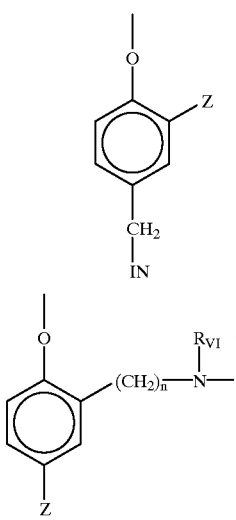

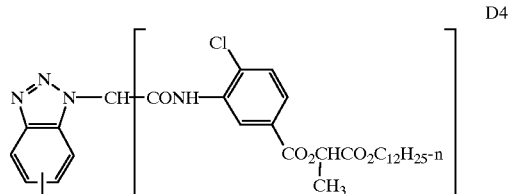

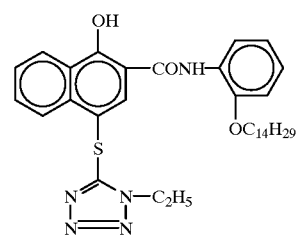

wherein IN is the inhibitor moiety, Z is selected from the group consisting of nitro, cyano, alkylsulfonyl; sulfamoyl (—SO$_2$NR$_2$); and sulfonamido (—NRSO$_2$R) groups; n is 0 or 1; and R$_{VI}$ is selected from the group consisting of substituted and unsubstituted alkyl and phenyl groups. The oxygen atom of each timing group is bonded to the coupling-off position of the respective coupler moiety of the DIAR.

Suitable developer inhibitor-releasing couplers for use in the present invention include, but are not limited to, the following:

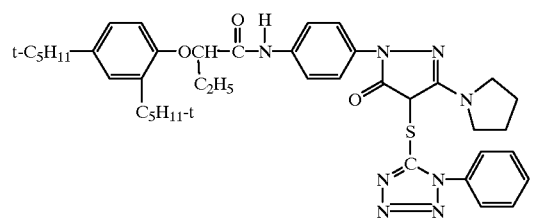

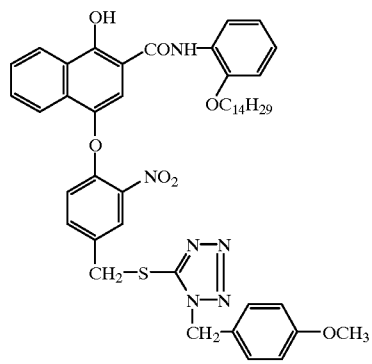

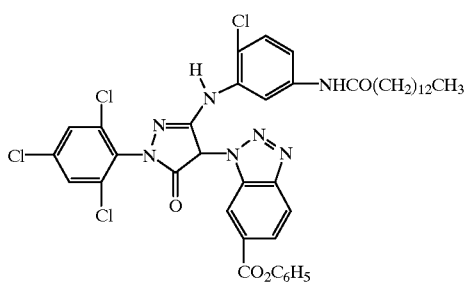

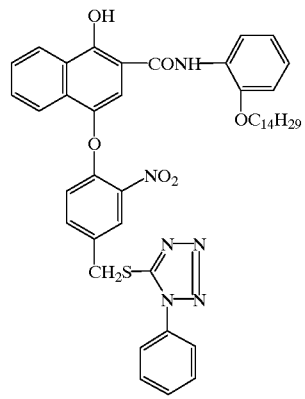

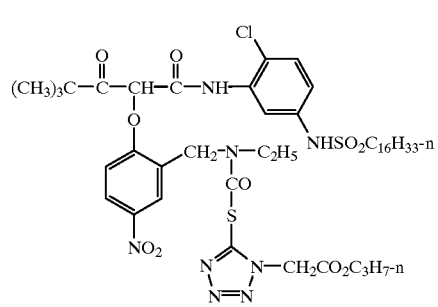

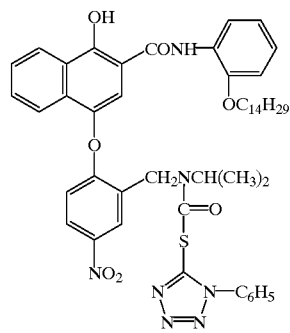

-continued

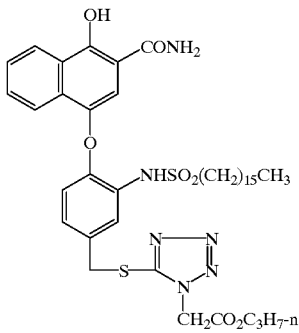

D9

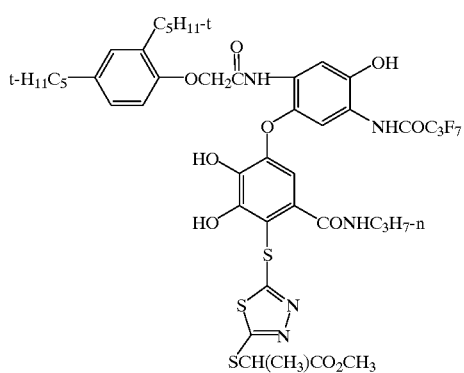

D10

It is also contemplated that the concepts of the present invention may be employed to obtain reflection color prints as described in *Research Disclosure,* November 1979, Item 18716, available from Kenneth Mason Publications, Ltd, Dudley Annex, 12a North Street, Emsworth, Hampshire P0101 7DQ, England, incorporated herein by reference. Materials of the invention may be coated on pH adjusted support as described in U.S. Pat. No. 4,917,994; on a support with reduced oxygen permeability (EP 553,339); with epoxy solvents (EP 164,961); with nickel complex stabilizers (U.S. Pat. Nos. 4,346,165; 4,540,653 and 4,906,559 for example); with ballasted chelating agents such as those in U.S. Pat. No. 4,994,359 to reduce sensitivity to polyvalent cations such as calcium; and with stain reducing compounds such as described in U.S. Pat. No. 5,068,171. Other compounds useful in combination with the invention are disclosed in Japanese Published Applications under the following Derwent accession numbers: 90-072,629; 90-072,630; 90-072,631; 90-072,632; 90-072,633; 90-072,634; 90-077,822; 90-078,229; 90-078,230; 90-079,336; 90-079,337; 90-079,338; 90-079,690; 90-079,691; 90-080,487; 90-080,488; 90-080,489; 90-080,490; 90-080,491; 90-080,492; 90-080,494; 90-085,928; 90-086,669; 90-086,670; 90-087,360; 90-087,361; 90-087,362; 90-087,363; 90-087,364; 90-088,097; 90-093,662; 90-093,663; 90-093,664; 90-093,665; 90-093,666; 90-093,668; 90-094,055; 90-094,056; 90-103,409; 83-62,586; 83-09,959.

If desired, the photographic element can be used in conjunction with an applied magnetic layer as described in *Research Disclosure,* November 1992, Item 34390 published by Kenneth Mason Publications, Ltd., Dudley Annex, 12a North Street, Emsworth, Hampshire P010 7DQ, ENGLAND. Thus, materials of the invention may be employed in conjunction with a photographic material where a relatively transparent film containing magnetic particles is incorporated into the material. The materials of this invention function well in such a combination and give excellent photographic results. Examples of such magnetic films are well known and are described for example in U.S. Pat. No. 4,990,276 and EP 459,349 which are incorporated herein by reference.

As disclosed in these publications, the particles can be of any type available such as ferro- and ferri-magnetic oxides, complex oxides with other metals, ferrites etc. and can assume known particulate shapes and sizes, may contain dopants, and may exhibit the pH values known in the art. The particles may be shell coated and may be applied over the range of typical laydown.

The embodiment is not limited with respect to binders, hardeners, antistatic agents, dispersing agents, plasticizers, lubricants and other known additives.

The couplers of the invention are especially suited for use in combination with these magnetic layers. The layer may suitably be located on the side of the photographic material substrate opposite to the silver halide emulsions and may be employed to magnetically record any desired information. One notable deficiency attributed to such a layer is that the particle layer tends to absorb blue light when light is shined through the processed negative to create a reflective color print. This distorts the color otherwise obtainable without the layer unless needed corrections are made. This also reduces the light transmission during printing so that the printing time must be increased for comparable results. In one embodiment of the invention, the coupler of the present invention may be incorporated in the magenta dye forming layer to replace all or part of the conventional coupler since the invention coupler contains less unwanted blue absorption and can therefore help counteract the undesirable impact of the magnetic layer. Also, if a yellow colored magenta mask is employed, the amount of the mask may be diminished. On the other hand, if all or a portion of the blue absorption can be tolerated, considering the reduction achieved by the invention, then additional amounts of photographically useful groups which generate dye with blue absorbance, such as development inhibitors, can be added to improve sharpness, color and other important photographic properties.

Especially useful in this invention are tabular grain silver halide emulsions. Specifically contemplated tabular grain emulsions are those in which greater than 50 percent of the total projected area of the emulsion grains are accounted for in the case of silver bromide or silver bromoiodide by tabular grains having a thickness of less than 0.3 micron (0.5 micron for blue sensitive emulsion) and an average tabularity (T) of greater than 25 (preferably greater than 100), where the term "tabularity" is employed in its art recognized usage as $$T=ECD/t^2$$

where

ECD is the average equivalent circular diameter of the tabular grains in micrometers and t is the average thickness in micrometers of the tabular grains.

The average useful ECD of photographic emulsions can range up to about 10 micrometers, although in practice emulsion ECD's seldom exceed about 4 micrometers. Since both photographic speed and granularity increase with increasing ECD's, it is generally preferred to employ the smallest tabular grain ECD's compatible with achieving aim speed requirements.

Emulsion tabularity increases markedly with reductions in tabular grain thickness. It is generally preferred that aim tabular grain projected areas be satisfied by thin (t<0.2 micrometers) tabular grains. To achieve the lowest levels of granularity it is preferred that aim tabular grain projected areas be satisfied with ultrathin (t<0.06 micrometers) tabular grains. Tabular grain thicknesses typically range down to about 0.02 micrometers. However, still lower tabular grain thicknesses are contemplated. For example, Daubendiek et al U.S. Pat. No. 4,672,027 reports a 3 mole percent iodide tabular grain silver bromoiodide emulsion having a grain thickness of 0.017 micronmeters. Ultrathin tabular grain high chloride emulsions are disclosed by Maskasky U.S. Pat. No. 5,217,858.

As noted above tabular grains of less than the specified thickness account for at least 50 percent of the total grain projected area of the emulsion. To maximize the advantages of high tabularity it is generally preferred that tabular grains satisfying the stated thickness criterion account for the highest conveniently attainable percentage of the total grain projected area of the emulsion. For example, in preferred emulsions, tabular grains satisfying the stated thickness criteria above account for at least 70 percent of the total grain projected area. In the highest performance tabular grain emulsions, tabular grains satisfying the thickness criteria above account for at least 90 percent of total grain projected area.

Suitable tabular grain emulsions can be selected from among a variety of conventional teachings, such as those of the following: Research Disclosure, Item 22534, January 1983, published by Kenneth Mason Publications, Ltd., Emsworth, Hampshire P010 7DD, England; U.S. Pat. Nos. 4,439,520; 4,414,310; 4,433,048; 4,643,966; 4,647,528; 4,665,012; 4,672,027; 4,678,745; 4,693,964; 4,713,320; 4,722,886; 4,755,456; 4,775,617; 4,797,354; 4,801,522; 4,806,461; 4,835,095; 4,853,322; 4,914,014; 4,962,015; 4,985,350; 5,061,069, 5,061,616, 5,210,013 and PCT Serial No. 93/06521, published Apr. 1, 1993.

The following examples are included for a further understanding of this invention.

EXAMPLE 1

Solubility and Dispersibility: The solubility was determined by addition of a known weight (0.2 g) of the given coupler to reagent grade ethyl acetate (0.6 g) in a vial and then stirring (5 min) at 25° C. Except for comparison couplers C-3, C-4, and C-5 (all CA-1 derivatives), all couplers dissolved immediately. Couplers C-3 and C-4 were insoluble in 0.6 g of ethyl acetate at 25° C. Additional quantities of ethyl acetate were added in increments to these three couplers. It required 4.5 g of ethyl acetate to dissolve 0.2 g of C-3 and 10.6 g of ethyl acetate to dissolve 0.2 g of C-4. Coupler C-5 (0.2 g) did not show any sign of solubility even after the addition of 10.8 g of ethyl acetate. The dispersibility characteristics of the couplers were determined by gently warming (50° C.) these solutions followed by addition of 4 ml of triisopropylnapthalene sulfonate, sodium salt (mixture of isomers) and gel to each vial. The resulting mixture was shaken vigorously and observed for any crystallization. All emulsified except C-3, C-4 and C-5.

These experiments clearly demonstrate the poor solubility/dispersibility characteristics of dialkylarylthio pyrazolones based on comparison parent CA-1. Unlike dialkylarylthio derivatives of CA-1 (C-3, C-4, and C-5), dialkylarylthio derivatives of parents claimed in the invention can be coated without resorting to washed dispersions or dimethylformamide addition. This is a significant and important improvement. While C-10 appears satisfactory in this test, it has unsatisfactory hue as shown in Table V. Table III shows these results.

TABLE III

| | Solubility/Dispersibility of the New Magenta Couplers | | |
|---|---|---|---|
| Coupler | Type | Solubility | Dispersibility |
| C-3 | Check | Poor | Poor |
| C-4 | Check | Poor | Poor |
| C-5 | Check | Poor | Poor |
| C-10 | Check | Good | Good |
| M-1 | Invention | Good | Good |

EXAMPLE 2

Reduction of Calcium Ion Sensitivity: The coupling kinetics of a number of coupler dispersions with oxidized color developer (4-Amino-3-methyl-N-ethyl-N-(β-methanesulfonamido)ethylaniline sesquisulfatesulfate hydrate,) are determined as a function of the calcium ion concentration by competition with the hydroxide deamination of the oxidized color developer. These competition kinetics are run in a buffer solution (0.0125 M of 4-carboxybenzenesulfonamide) containing a maximum of 0.36 M potassium ion and a series of calcium ion concentrations (from 0 to 0.16 M) with varying potassium ion to maintain a constant total cation level. Known, limited amounts of color developer and excess oxidant (potassium ferricyanide) are added to the dilute dispersions in the buffered media. The relative dye yields are determined spectrophotometrically as a function of the coupler concentration. After corrections for interfering densities, the coupling rate constants are calculated from previously determined rates for oxidized developer deamination as a function of pH by use of standard competition kinetics analysis. For each coupler dispersion the log of the coupling rate constant is plotted as a function of the log of the calcium ion concentration. For all of these coupler dispersions there is a region wherein the coupling rate constants are independent of calcium ion concentration ($k_1$) and a region of decreasing coupling rate with increasing calcium ion concentration. The point of intersection of the calcium ion dependent region and the calcium ion independent region is defined as the threshold, and is reported as the log of the calcium ion concentration for that point. The relative threshold normalizes the values with respect to check coupler C-1. Couplers with a relative threshold of less than 1.0 are more sensitive to calcium ion than couplers with a relative threshold of greater than 1.0. The threshold, the absolute rate constants with no added calcium ion ($k_1$), at a calcium ion concentration of 0.1 M ($k_2$), and the difference ($\Delta \log k$) are presented in Table IV below. From this information is calculated a relative sensitivity toward calcium ion by normalizing the $\Delta \log k$ information with respect to check coupler C-1. Couplers with a relative sensitivity of greater than 1.0 are more sensitive toward calcium ion than couplers with a relative sensitivity of less than 1.0.

As is clearly seen, couplers represented by the invention are less sensitive to the presence of calcium ion in the process than the check couplers. For instance, in comparison to check coupler C-1, invention coupler M-4 has a threshold value 79 times larger, and is more than 4 times less sensitive toward calcium ion at a concentration of 0.1 M.

TABLE IV

| Coupler (Type) | Threshold | Relative Threshold | log $k_1$ | log $k_2$ | Δ log k | Relative Sensitivity |
|---|---|---|---|---|---|---|
| | | Relative Reactivity in the Presence of Calcium Ion | | | | |
| C-1 (check) | −4.3 | 1.0 | 2.34 | 1.22 | −1.12 | 1.0 |
| C-2 (check) | −5.3 | 0.1 | 2.90 | 1.33 | −1.57 | −2.8 |
| C-9 (check) | −4.5 | 0.6 | 3.05 | 1.42 | −1.63 | 3.2 |
| M-2 (Invention) | −2.8 | 32 | 3.81 | 2.84 | −0.97 | 0.71 |
| M-4 (Invention) | −2.4 | 79 | 3.11 | 2.60 | −0.51 | 0.25 |

Coating Method 1: Photographic elements were prepared by coating a gel-subbed, polyethylene-coated paper support with a photosensitive layer containing a silver chlorobromide emulsion at 0.168 g Ag/m² (or 0.337 g for 4-equivalent couplers) gelatin at 1.62 g/m², and the magenta image coupler at 0.38 mmol/m² dispersed in dibutyl phlthalate (half the weight of the coupler). Each coupler dispersion also contained the following addenda (weight percent of coupler): Addendum-1 (200%), Addendum-2 (10%). The photosensitive layer was overcoated with a protective layer containing gelatin at 1.08 g/m² and bisvinylsulfonylmethyl ether hardener at 2 weight percent based on total gelatin.

Coating Method 2: Photographic elements were prepared by coating a gel-subbed, polyethylene-coated paper support with a photosensitive layer containing a silver chlorobromide emulsion at 0.172 g Ag/m² (or 0.2865 for 4-equivalent couplers), gelatin at 1.238 g/m², and a magenta image coupler indicated below at 0.38 mmol/m² dispersed in an equal weight of tricresyl phosphate. Each coupler dispersion also contained the following addenda (weight percent of coupler): Addendum-3 (48%), Addendum-4 (29%), Addendum-5 (32%), Addendum-6 (16%). The photosensitive layer was overcoated with a protective layer containing gelatin at 1.08 g/m² and bisvinylsulfonylmethyl ether hardener at 2 weight percent based on total gelatin.

Coating Method 3: Photographic elements were prepared by coating a gel-subbed, polyethylene-coated paper support with a photosensitive layer containing a silver chloride emulsion at 0.172 g Ag/m² (or 0.2865 for 4-equivalent couplers), gelatin at 1.238 g/m², and a magenta image coupler indicated below at 0.38 mmol/m² dispersed in an equal weight of tricresyl phosphate. Each coupler dispersion also contained the following addenda (weight percent of coupler): Addendum-3 (48%), Addendum-4 (29%), Addendum-5 (32%), Addendum-6 (16%). The photosensitive layer was overcoated with a protective layer containing gelatin at 1.08 g/m² and bisvinylsulfonylmethyl ether hardener at 2 weight percent based on total gelatin.

Coating Method 4 (2-Equivalent Couplers): Photographic elements were prepared by coating a gel-subbed, polyethylene-coated paper support with a photosensitive layer containing a silver chloride emulsion at 0.172 g Ag/m², gelatin at 1.615 g/m², and a magenta image coupler indicated below at 0.329 mmol/m² dispersed in the following addenda (weight percent of coupler): tricresyl phosphate (100%), Addendum-5 (116.7%), and Addendum-6 (16.7%). The photosensitive layer was overcoated with (1) an ultraviolet-absorbing layer containing gelatin at 1.33 g/m², 2-(2H-benzotriazol-2-yl)-2, 4-bis-(1, 1-dimethylpropyl)phenol at 0.732 g/m² and 2-(5-chloro-2H-benzotriazol-2-yl)-4-methyl-6-t-butyl)phenol at 0.129 g/m², and (2) a protective layer containing gelatin at 1.40 g/m² and bisvinylsulfonylmethyl ether hardener at 1.77 weight percent based on total gelatin. The levels of coupler and silver were chosen to approximate the sensitometry of the 4-equivalent check coupler.

Addendum-1:

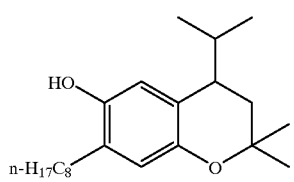

Addendum-2:

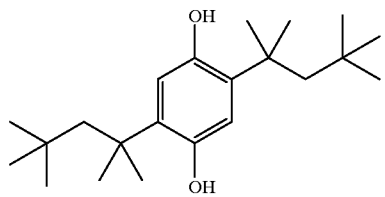

Addendum-3: (Compound No. I-1 in U.S. Pat. No. 4,217, 410)

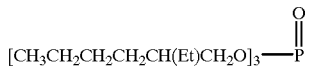

Addendum-4: (Compound No. 21 in U.S. Pat. No. 4,360, 589)

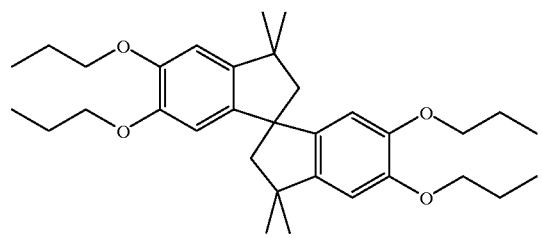

Addendum-5: (Compound No. II-10 in EP 81,768)

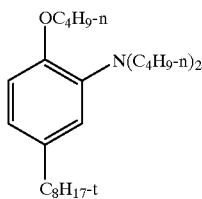

Addendum-6: (Compound No. 104 in EP 69,070)

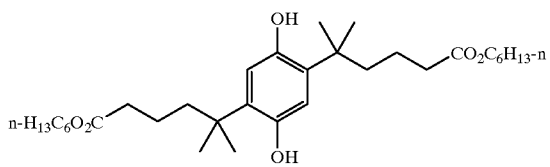

Process Method 1: Samples of each element were imagewise exposed through a graduated-density test object, processed in color developer 1 at 33° C. for 3.25 minutes in the color developer, 1.5 minutes in the bleach-fix bath, washed and dried.

Process Method 2: Samples of each element were imagewise exposed through a graduated density test object, then processed in color developer 2 at 35° C. (45 seconds in a color developer, 45 seconds in the bleach-fix bath of Examples 1–3) washed and dried.

Color Developer 1 (pH 10.08)

| | |
|---|---|
| Triethanolamine | 11 mL |
| Benzyl alcohol | 14.02 mL |
| Lithium chloride | 2.0 g |
| Potassium bromide | 0.6 g |
| Hydroxylamine sulfate | 3.2 g |
| Potassium sulfite (45% solution) | 2.8 mL |
| 1-Hydroxyethylidene-1,1-di-phosphonic acid (60%) | 0.8 mL |
| 4-Amino-3-methyl-N-ethyl-N-(β-methanesulfonamido) ethylaniline sesquisulfate hydrate | 4.35 g |
| Potassium carbonate (anhydrous) | 28 g |
| Stilbene whitening agent | 0.6 g |
| Surfactant | 1 mL |
| Water to make | 1.0 L |

Color Developer 2 (pH 10.04)

| | |
|---|---|
| Triethanolamine | 12.41 g |
| Lithium sulfate | 2.70 g |
| N,N-Diethylhydroxylamine (85% solution) | 5.40 g |
| 1-Hydroxyethylidene-1,1-di-phosphonic acid (60%) | 1.16 g |
| 4-Amino-3-methyl-N-ethyl-N-(β-methanesulfonamido) ethylanilinesesquisulfate hydrate | 5.00 g |
| Potassium carbonate (anhydrous) | 21.16 g |
| Potassium bicarbonate | 2.79 g |
| Potassium chloride | 1.60 g |
| Potassium bromide | 7.0 mg |
| Stilbene whitening agent | 2.30 g |
| Surfactant | 1 mL |
| Water to make | 1.0 L |

Bleach-Fix Bath (pH 6.8)

| | |
|---|---|
| Ammonium thiosulfate | 104 g |
| Sodium hydrogen sulfite | 13 g |
| Ferric ammonium ethylenediamine tetraacetic acid (EDTA) | 65.5 g |
| EDTA | 6.56 g |
| Ammonium hydroxide (28%) | 27.9 mL |
| Water to make | 1 L |

EXAMPLE 3

Hue—The spectral characteristics (λmax) for the 4-amino-3-methyl-N-ethyl-N-β-(methanesulfonamido) ethylaniline dyes of the representative couplers are summarized in Table V. It is clearly evident that the dye hues of M-1 through M-6 are bathochromic relative to the dye hue obtained from the comparison couplers. Bathochromic dye hues are desirable for better color reproduction.

TABLE V

Spectral Characteristics of the Magenta Dyes

| Coupler | λmax (nm) | Coating Method | Process Method | Type |
|---|---|---|---|---|
| C-1 | 536 | 3 | 2 | Check |
| C-2 | 536 | 3 | 2 | Check |
| C-6 | 537 | 2 | 1 | Check |
| C-7 | 537 | 3 | 2 | Check |
| C-8 | 536 | 3 | 2 | Check |
| C-9 | 536 | 2 | 1 | Check |
| C-10 | 539 | 2 | 1 | Check |
| M-1 | 543 | 2 | 1 | Invention |
| M-2 | 542 | 2 | 1 | Invention |
| M-3 | 542 | 2 | 1 | Invention |
| M-4 | 543 | 4 | 2 | Invention |
| M-5 | 543 | 4 | 2 | Invention |
| M-6 | 543 | 4 | 2 | Invention |

EXAMPLE 4

Thermal Stability: Comparison 4-equivalent couplers were coated by Method 1 and couplers of the invention were coated by Method 2. Both were processed by Method 1, and the data obtained after treatment under the specified conditions is listed in Table VI. It is clearly evident that couplers of the invention are much less prone to discoloration than the check couplers with the apparent exception of C-10. However, C-10 exhibits poor hue as shown by Table V.

TABLE VI

Thermal Stability of the Magenta Dyes[a,b]

| | | Dmin Yellowing (Initial D = 0) | | Dye Fade (Initial D = 1.0) | |
|---|---|---|---|---|---|
| Coupler | Type | Dry | Wet | Dry | Wet |
| CA-2 (Q = H) | Check | 9 | 19 | −8 | 0 |
| CA-3 (Q = H) | Check | 10 | 27 | −15 | 6 |
| A-1 (Q = H) | Check | 14 | 30 | −16 | 6 |
| A-3 (Q = H) | Check | 22 | 39 | −9 | 11 |
| C-10 | Check | 5 | 3 | 1 | −1 |
| M-1 | Invention | 7 | 7 | 3 | 2 |

[a]Dry Oven Conditions: 2 weeks at 77° C./15% relative humidity.
[b]Wet Oven Conditions: 2 weeks at 60° C./70% relative humidity.

EXAMPLE 5

The invention coupler M-2 and comparison coupler C-1 were coated using Method 3 and processed using Method 2. The processed coatings were exposed to heat and the results are tabulated below in Table VII. The large increases in density for the check coupler are indicative of the decomposition of a stable leuco-dye to give additional magenta dye upon heat treatment. The couplers of the invention do not form a stable leuco-dyes under these rapid access conditions. Therefore, couplers of the invention do not require Lippman fine grain silver halide for rapid machine processing, a distinct advantage over comparison coupler C-1.

TABLE VII

Unwanted Formation of Stable Leuco-Dyes[a,b]

| Coupler | Type | 1 Week Fade (Initial D = 1.7) | | 2 Week Fade (Initial D = 1.7) | |
|---|---|---|---|---|---|
| | | Dry | Wet | Dry | Wet |
| C-1 | Check | 33 | 34 | 31 | 32 |
| M-2 | Invention | 2 | 5 | 2 | 4 |

[a]Dry Oven Conditions: 77° C./15% relative humidity.
[b]Wet Oven Conditions: 60° C./70% relative humidity.

EXAMPLE 6

(Comparison)

A photographic element was produced by coating the following layers on a cellulose triacetate film support (coverage are in grams per meter squared, emulsion sizes as determined by the disc centrifuge method and are reported in Diameter×Thickness in microns);

Layer 1 (Antihalation layer): black collodial silver sol at 0.140; gelatin at 2.15; OxDS-1 at 0.108, DYE-1 at 0.049; DYE-2 at 0.017 and DYE-3 at 0.014.

Layer 2 (Slow cyan layer): a blend of three red sensitized (all with a mixture of RSD-1 and RSD-2) silver iodobromide emulsions: (i) a large sized tabular grain emulsion (1.3× 0.118, 4.1 mole % I) at 0.522 (ii) a smaller tabular emulsion (0.85×0.115, 4.1 mole % I) at 0.337 and (iii) a very small tabular grain emulsion (0.55×0.115, 1.5 mole % I) at 0.559; gelatin at 2.85; cyan dye-forming coupler CC-1 at 0.452; DIR coupler DIR-1 at 0.043; bleach accelerator releasing coupler B-1 at 0.054 and anti-foggant 4-hydroxy-6-methyl-1,3,3a,7-tetraazaindene at 0.016.

Layer 3 (Fast cyan layer): a red-sensitized (same as above) tabular silver iodobromide emulsion (2.2×0.128, 4.1 mole % I) at 0.086; cyan coupler CC-1 at 0.081; DIR-1 at 0.034; MC-1 at 0.043; gelatin at 1.72 and anti-foggant 4-hydroxy-6-methyl-1,3,3a,7-tetraazaindene at 0.010.

Layer 4 (Interlayer): gelatin at 1.29.

Layer 5 (Slow magenta layer): a blend of two green sensitized (both with a mixture of GSD-1 and GSD-2) silver iodobromide emulsions: (i) 0.54×0.091, 4.1 mole % iodide at 0.194 and (ii) 0.52×0.085, 1.5 mole % iodide at 0.559; magenta dye forming coupler CM-1 at 0.258; gelatin at 1.08 and anti-foggant 4-hydroxy-6-methyl-1,3,3a,7-tetraazaindene at 0.005.

Layer 6 (Mid magenta layer): a blend of two green sensitized (same as above) tabular silver iodobromide emulsions (i) 1.3×0.113, 4.1 mole % I at 0.430 and (ii) 0.54×0.91, 4.1 mole % I at 0.172; Coupler CM-1 at 0.086; MC-2 at 0.151; DIR-2 at 0.016; gelatin at 2.12 and anti-foggant 4-hydroxy-6-methyl-1,3,3a,7-tetraazaindene at 0.003.

Layer 7 (Fast magenta layer): a green sensitized tabular silver iodobromide (1.8×0.127, 4.1 mole % I) emulsion at 0.689; gelatin at 1.61; Coupler CM-1 at 0.059; MC-2 at 0.054 and DIR-3 at 0.003.

Layer 8 (Yellow filter layer): gelatin at 0.86; Carey-Lea silver at 0.043 and OxDS-2 at 0.054.

Layer 9 (Slow yellow layer): an equal blend of three blue sensitized (both with BSD-1) tabular silver iodobromide emulsions (i) 0.50×0.085, 1.5 mole % I (ii) 0.60 diameter, 3% mole I and (iii) 0.68 diameter, 3 mole % I at a total of 0.430; yellow dye forming coupler CY-1 at 0.699; CY-2 at 0.215; DIR-4 at 0.086; CC-1 at 0.097 and gelatin at 2.066.

Layer 10 (Fast yellow layer): two blue sensitized (with BSD-1) tabular silver iodobromide emulsions (i) 3.1×0.137, 4.1 mole % I at 0.396 (ii) 0.95 diameter, 7.1 mole % I at 0.47; CY-1 at 0.131; CY-2 at 0.215; DIR-4 at 0.075; CC-1 at 0.011; B-1 at 0.008 and gelatin at 1.08.

Layer 11 (Protective overcoat and UV filter layer): gelatin at 1.61; silver bromide Lippman emulsion at 0.215; UV-1 and UV-2 (1:1 ratio) at a total of 0.023 and bis (vinylsulfonyl)methane hardener at 1.6% of total gelatin weight.

Surfactants, coating aids, emulsion addenda, sequestrants, lubricants, matte and tinting dyes were added to the appropriate layers as is common in the art.

EXAMPLE 7

(Invention)

Example 7 was prepared in a similar manner as Example 6, except that Coupler CM-1 in layers 5, 6 and 7 was replaced with Coupler M-5 of the invention at 0.054, 0.081 and 0.215, respectively.

Samples of each element were exposed imagewise in all three colors through a stepped density test object and subjected to the KODAK FLEXICOLOR (C41) process as described in *British Journal of Photography Annual,* 1988, pp 196–198. In TABLE VIII, all data is for the green record. Gamma refers to the maximum slope between any two adjacent density steps. Acutance is the MTF at 50 cycles/mm. Granularity is the RMS granularity at midscale (the step closest to +1.2 log E units above the Dmin) divided by the instantaneous gamma at that step (see U.S. Pat. No. 4,912,024).

TABLE VIII

MULTILAYER RESULTS

| Sample | Coupler | Dmin | Dmax | Gamma | Acutance | Granularity |
|---|---|---|---|---|---|---|
| 1 | CM-1 | .587 | 2.496 | .773 | .573 | 19.4 |
| 2 | M-5 | .595 | 2.592 | .814 | .583 | 18.6 |

The above data clearly indicates that a coupler of the invention gives excellent performance in a negative multilayer format with improvements in both acutance and granularity relative to a related 5-pyrazolone magenta image coupler.

DYE-1:

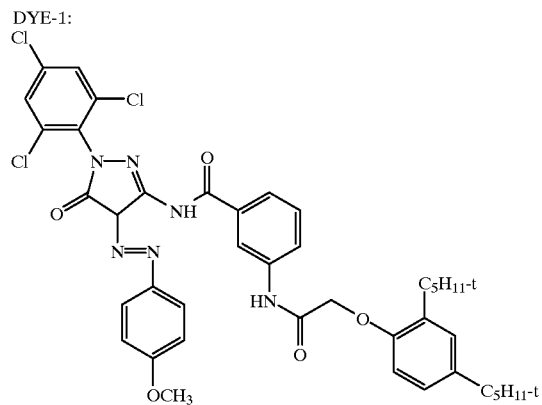

DYE-2:
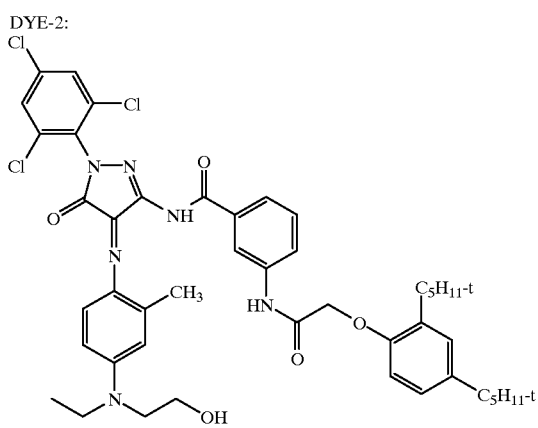
DYE-3:
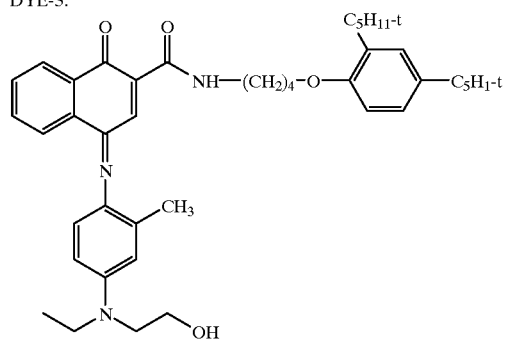
CC-1:
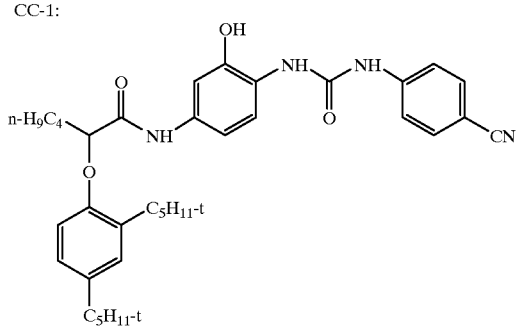
CM-1
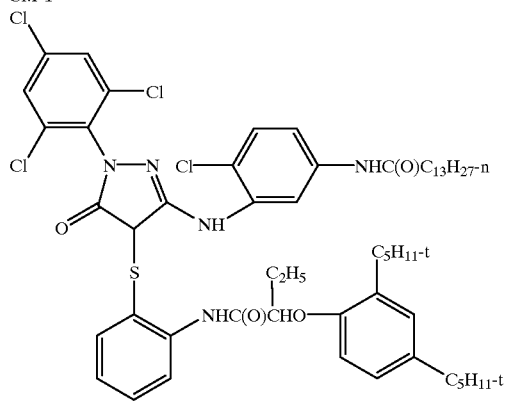
CY-1:
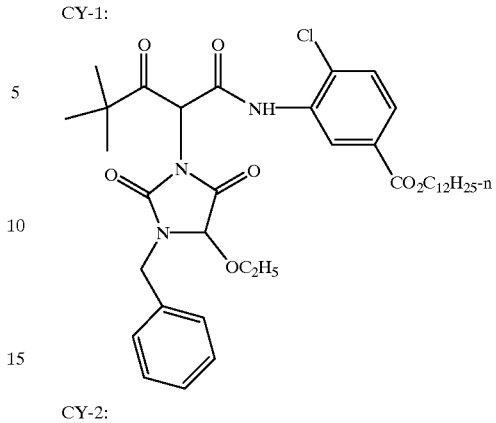
CY-2:
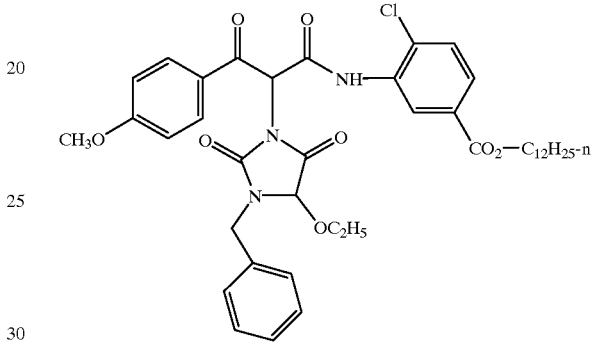
DIR-1:
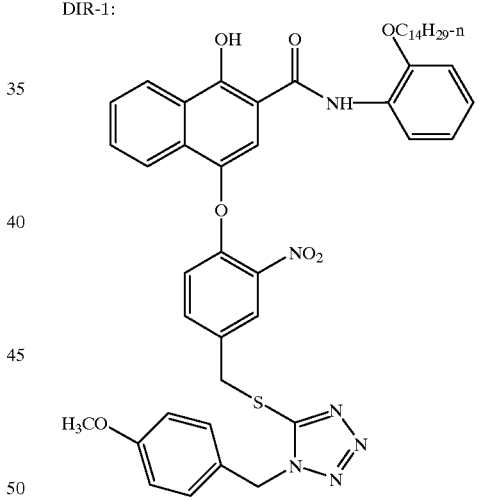
DIR-2:
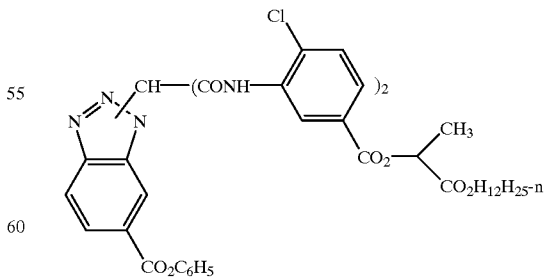

DIR-3:
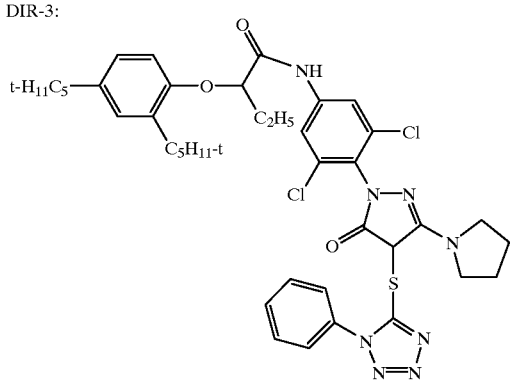
DIR-4:
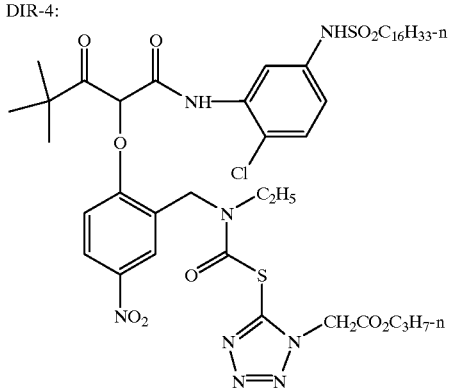
MC-1:
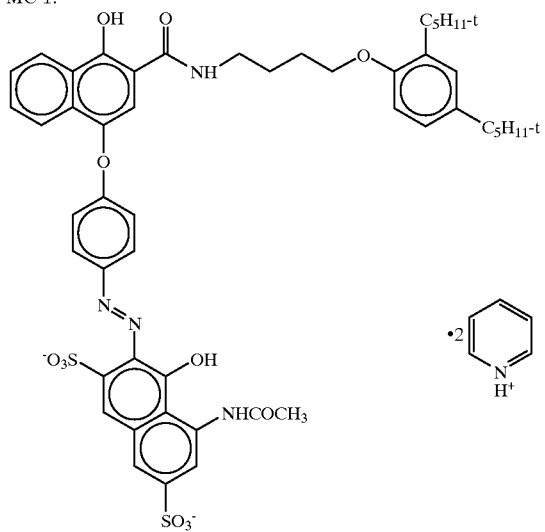
MC-2:
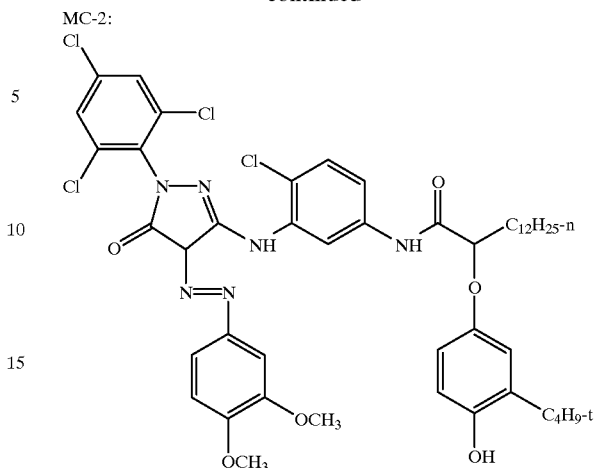
B-1:
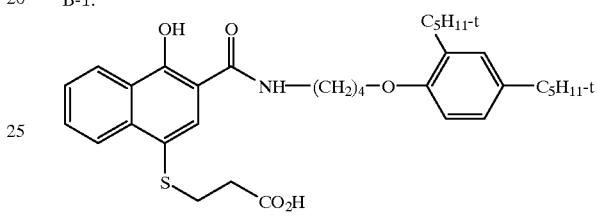
OxDS-1:
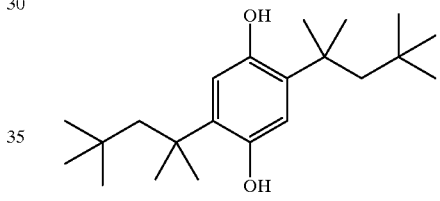
OXDS-2:
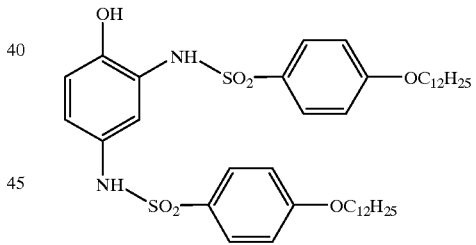
UV-1:
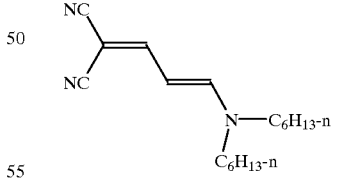
UV-2:
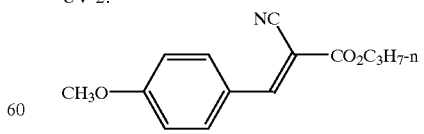

43

-continued

RSD-1:
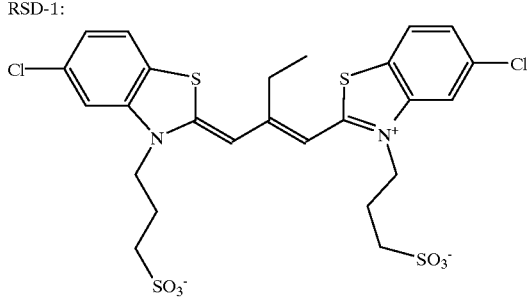

RSD-2:
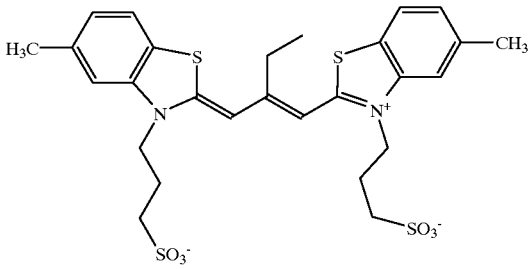

GSD-1:
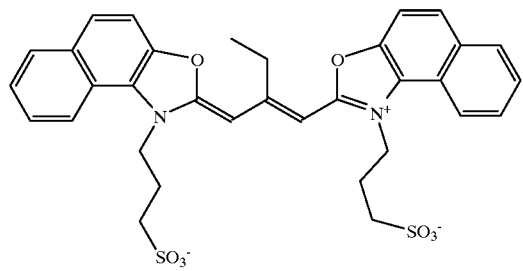

GSD-2:
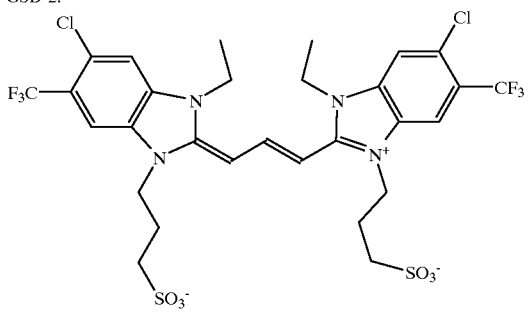

BSD-1:
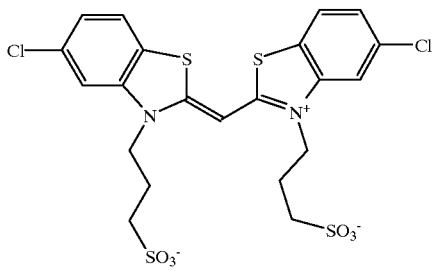

The invention has been described in detail with particular reference to preferred embodiments thereof, but it will be understood that variations and modifications can be effected within the spirit and scope of the invention.

What is claimed is:

1. A photographic element comprising at least one photosensitive silver halide emulsion layer having associated

44 therewith a 5-pyrazolone photographic coupler represented by the formula:

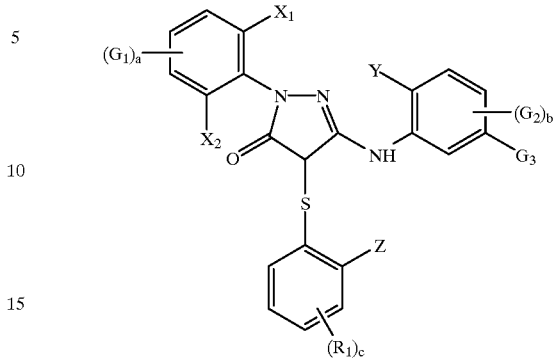

wherein:
a) substituents $X_1$, $X_2$, Y, $G_1$, and $G_2$ are individually selected from the group consisting of halogen, alkyl, alkoxy, aryloxy, acylamino, alkylthio, arylthio, sulfonamido, sulfamoyl, sulfamido, carbamoyl, diacylamino, alkoxycarbonyl, aryloxycarbonyl, alkoxysulfonyl, aryloxysulfonyl, alkylsulfonyl, arylsulfonyl, alkylsulfinyl, arylsulfinyl, alkoxycarbonylamino, aryloxycarbonylamino, alkylureido, arylureido, acyloxy, nitro, trifluoromethyl and carboxy and, in the case of $X_1$, $X_2$, and Y, hydrogen;
b) a, b, and c are individually integers form 0 to 3 provided that "a" cannot be an integer which, combined with the selection of $X_1$ and $X_2$, allows the number of chloride substituents on the ring containing $G_1$ to exceed 3;
c) $G_3$ is selected from the group consisting of hydrogen, halogen, acylamino, sulfonamido, sulfamido, carbamoyl, diacylamino, alkoxycarbonyl, aryloxycarbonyl, alkoxysulfonyl, aryloxysulfonyl, alkylsulfonyl, arylsulfonyl, alkylsulfinyl, arylsulfinyl, alkoxycarbonylamino, aryloxycarbonylamino, alkylureido, arylureido, acyloxy, trifluoromethyl and carboxyl;
d) $R_1$ is selected from the group consisting of $G_1$ and hydroxyl;
e) Z is an alkyl group containing at least 3 carbon atoms; and
f) the sum of the Hammett's sigma values for $X_1$, $X_2$, Y, $G_1$, $G_2$, and $G_3$ is at least 1.3.

2. The element of claim 1 wherein the substituents $X_1$, $X_2$, Y, $G_1$, $G_2$, are individually selected from the group consisting of chloride, fluoride, acylamino, sulfonamido, sulfamoyl, carbamoyl, alkoxycarbonyl, aryloxycarbonyl, alkylsulfonyl, arylsulfonyl, alkoxycarbonylamino, aryloxycarbonylamino, alkylureido, arylureido, and trifluoromethyl.

3. The element of claim 2 wherein $X_1$, $X_2$ and Y are chloride.

4. The element of claim 3 wherein $G_1$ and $G_2$ are individually selected from the group consisting of chloride, fluoride, acylamino, sulfonamido, sulfamoyl, carbamoyl, alkoxycarbonyl, aryloxycarbonyl, alkylsulfonyl, arylsulfonyl and trifluoromethyl.

5. The element of claim 1 wherein Z is an alkyl group of not more that 30 carbon atoms.

6. The element of claim 5 wherein Z contains less than 20 carbon atoms.

7. The element of claim 5 wherein Z is a branched chain alkyl group.

8. The element of claim 1 wherein the sum of the carbon atoms in Z and $R_1$ totals at least six.

9. The element of claim 1 wherein $G_1$ is para to the pyrazolone ring.

10. The element of claim 1 wherein c is at least 1 and wherein $R_1$ is an alkyl group of at least 3 atoms.

11. The element of claim 10 wherein both Z and $R_1$ are branched chain alkyl groups.

12. The element of claim 1 wherein the substituents on the arylthio group are free of alkoxy groups.

13. The element of claim 1 additionally containing at least one addendum having a structure selected from the following:

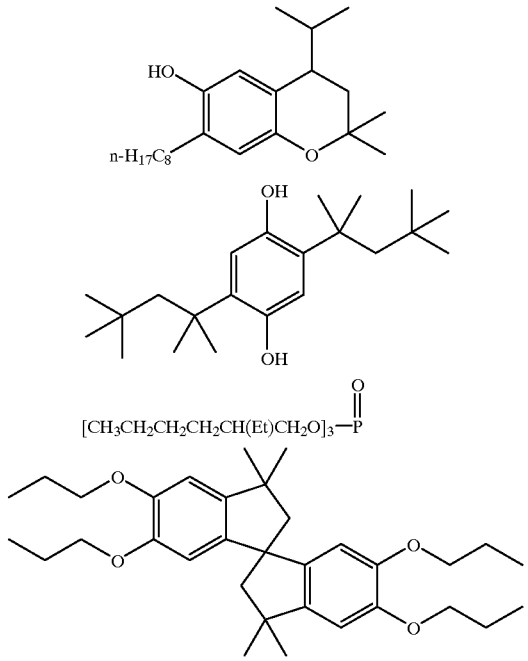

-continued

14. The element of claim 1 wherein the photographic element additionally comprises a layer of magnetic particles.

15. The element of claim 14 additionally comprising masking material which is yellow in unexposed areas following development.

16. A process of forming a photographic image which comprises developing an exposed silver halide emulsion layer with a color developing agent in the presence of a coupler as described in claim 1.

17. A process for reducing the unwanted blue absorption of a multicolor photographic material having a support bearing a photosensitive silver halide emulsion layer for magenta dye formation, the process comprising using a coupler having the structure of claim 1 in an emulsion layer responsible for magenta dye formation.

18. The element of any one of claims 1 through 15 wherein the sum of the Hammett's sigma values for $X_1$, $X_2$, Y, $G_1$, $G_2$, and $G_3$ is at least 1.4.

19. The element of any one of claims 1 through 15 wherein the sum of the Hammett's sigma values for $X_1$, $X_2$, Y, $G_1$, $G_2$, and $G_3$ is at least 1.5.

* * * * *